United States Patent
Bitoun et al.

(10) Patent No.: US 10,947,540 B2
(45) Date of Patent: Mar. 16, 2021

(54) ALLELE-SPECIFIC SILENCING THERAPY FOR DYNAMIN 2-RELATED DISEASES

(71) Applicants: ASSOCIATION INSTITUT DE MYOLOGIE, Paris (FR); INSTITUT NATIONAL DE LA SANTÉ ET DE LA RECHERCHE MÉDICALE, Paris (FR); SORBONNE UNIVERSITE, Paris (FR); CENTRE NATIONAL DE LA RECHERCHE SCIENTIFIQUE, Paris (FR)

(72) Inventors: Marc Bitoun, Villejuif (FR); Delphine Trochet, Villejuif (FR); Bernard Prudhon, Paris (FR)

(73) Assignees: ASSOCIATION INSTITUT DE MYOLOGIE, Paris (FR); INSERM (INSTITUT NATIONAL DE LA SANTÉ ET DE LA RECHERCHE MÉDICALE, Paris (FR); SORBONNE UNIVERSITE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/464,482

(22) PCT Filed: Nov. 19, 2017

(86) PCT No.: PCT/EP2017/080884
§ 371 (c)(1),
(2) Date: May 28, 2019

(87) PCT Pub. No.: WO2018/100010
PCT Pub. Date: Jun. 7, 2018

(65) Prior Publication Data
US 2019/0309305 A1 Oct. 10, 2019

(30) Foreign Application Priority Data

Nov. 29, 2016 (EP) .................................... 16306575

(51) Int. Cl.
*C12N 15/113* (2010.01)

(52) U.S. Cl.
CPC ...... *C12N 15/1137* (2013.01); *C12N 2310/14* (2013.01); *C12N 2320/34* (2013.01); *C12Y 306/05005* (2013.01)

(58) Field of Classification Search
None
See application file for complete search history.

(56) References Cited

U.S. PATENT DOCUMENTS

2016/0230169 A1* 8/2016 Davidson ............. C12N 15/113
2016/0264976 A1* 9/2016 Laporte .................. A61P 43/00

FOREIGN PATENT DOCUMENTS

WO WO-2004070062 A2 * 8/2004 ........... C12N 15/117
WO WO-2015055859 A1 * 4/2015 .............. A61P 43/00

OTHER PUBLICATIONS

Cowling BS, Chevremont T, Prokic I, et al (2014) Reducing dynamin 2 expression rescues X-linked centronuclear myopathy. J Clin Invest 124:1350-63 (Year: 2014).*
Tasfaout H, Buono S, Guo S, et al (2017) Antisense oligonucleotide-mediated Dnm2 knockdown prevents and reverts myotubular myopathy in mice. (Year: 2017).*
Tinelli E, Pereira JA, Suter U (2013) Muscle-specific function of the centronuclear myopathy and Charcot-Marie-Tooth neuropathy-associated dynamin 2 is required for proper lipid metabolism, mitochondria, muscle fibers, neuromuscular junctions and peripheral nerves. Hum Mol Genet 22:4417-29 (Year: 2013).*
Ferguson S, Raimondi A, Paradise S, et al (2009) Coordinated actions of actin and BAR proteins upstream of dynamin at endocytic clathrin-coated pits. Dev Cell 17:811-22 (Year: 2009).*
Alexander MS, Kawahara G, Motohashi N, et al (2013) MicroRNA-199a is induced in dystrophic muscle and affects WNT signaling, cell proliferation, and myogenic differentiation. Cell Death Differ 20:1194-208. (Year: 2013).*
Tasfaout H, Lionello V, Kretz CM, et al (2018) Single intramuscular injection of AAV-shRNA reduces DNM2 and prevents myotubular myopathy in mice. Mol Ther (Year: 2018).*

* cited by examiner

*Primary Examiner* — Brian Whiteman
(74) *Attorney, Agent, or Firm* — W&C IP

(57) ABSTRACT

The invention relates to an allele specific siRNA able to silence the expression of only one allele of a heterozygous DNM2 gene, for treating diseases caused by heterozygous mutation and/or overexpression of Dynamin 2.

Figure 1:
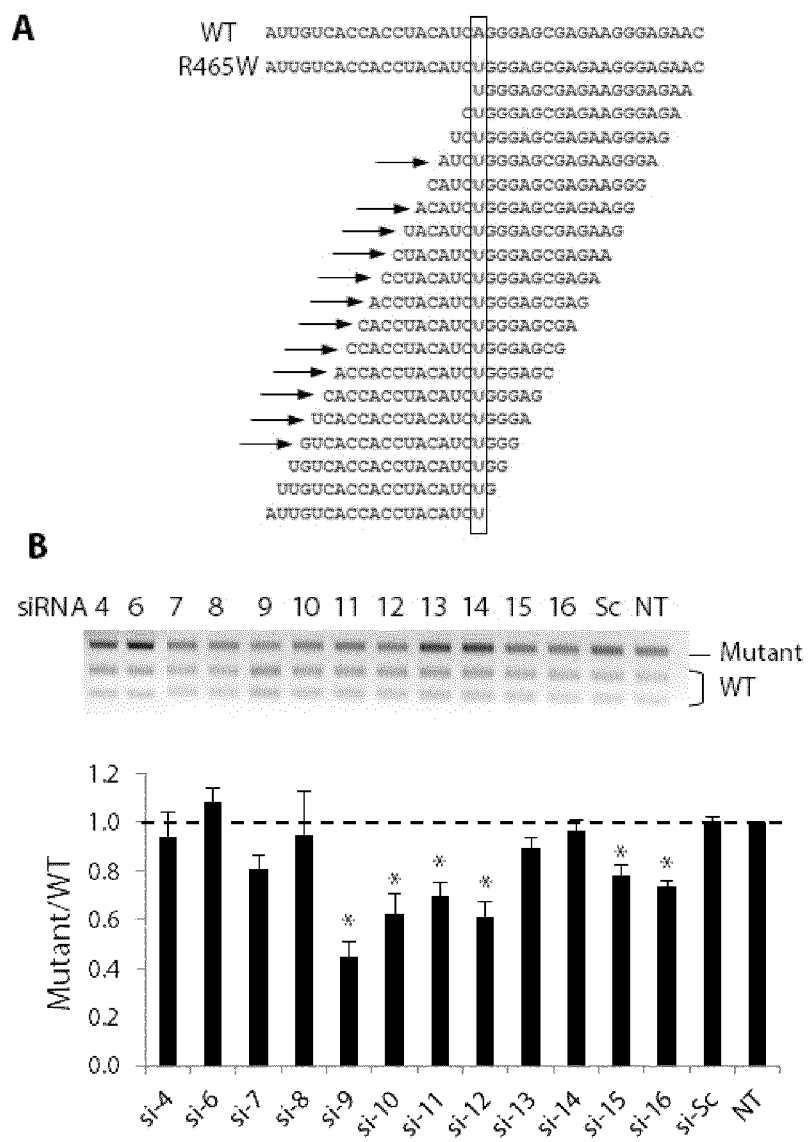

13 Claims, 11 Drawing Sheets
Specification includes a Sequence Listing.

| Age/treatment duration (mo) | | | | |
|---|---|---|---|---|
| | | 1/3 | | |
| genotype | WT | HTZ | | |
| treatment | - | noSh | Sh9 | Sh10 |
| mass (mg) | 49.8±0.9 | 36.1±1.7[b] | 46.5±0.9[a,e] | 41.3±1.3[b,c] |
| PO (g) | 114.2±2.4 | 70.2±3.0[b] | 107.9±3.6[e] | 84.8±3.6[b,d] |
| sPO (g/mg) | 2.3±0.1 | 2.0±0.1[a] | 2.3±0.1[c] | 2.1±0.1[a,d] |
| n | 8 | 8 | 8 | 8 |

Figure 4

A

B

ALLELE-SPECIFIC SILENCING THERAPY FOR DYNAMIN 2-RELATED DISEASES

FIELD OF THE INVENTION

The present invention relates to an allele specific siRNA able to silence the expression of only one allele of a heterozygous DNM2 gene, for treating diseases caused by heterozygous mutation and/or overexpression of Dynamin 2.

BACKGROUND

Dynamin 2 is a ubiquitously expressed protein that belongs to the superfamily of large GTPases. Dynamin 2 (DNM2) acts as a mechanochemical scaffolding molecule that deforms biological membranes leading to the release of nascent vesicles. At the plasma membrane DNM2 is involved in clathrin-dependent and clathrin-independent endocytosis. This protein is also involved in the formation of vesicles from endosomes and trans-Golgi network. Several studies have highlighted the role of Dynamin 2 as regulator of actin and microtubule cytoskeletons.

Several dominant genetic diseases are caused by heterozygous mutations of the DNM2 gene coding for said Dynamin 2 protein. In particular, autosomal dominant centronuclear myopathy (AD-CNM) results from mutations in the DNM2 gene. AD-CNM is a rare congenital myopathy characterized by the high incidence of centrally placed nuclei in muscle fibers in absence of regenerative process. The AD-CNM is associated with a wide clinical spectrum from severe-neonatal to mild-adult forms. In general, motor milestones are delayed and diffuse skeletal muscle weakness mainly involves facial and limb muscles. Muscle weakness is slowly progressive but loss of independent ambulation may occur during the fifth decade. In the severe and early-onset CNM, paediatric patients usually have generalized weakness, hypotonia, moderate degree of facial weakness with open mouth, ptosis and ophthalmoplegia. No curative treatment is available for the AD-CNM.

Mutations in the DNM2 gene are also involved in rare cases of Charcot-Marie-Tooth disease and Hereditary Spastic Paraplegia. Charcot-Marie-Tooth disease (CMT) is a hereditary motor and sensory neuropathy characterized by progressive loss of muscle tissue and touch sensation across various parts of the body. Hereditary spastic paraplegia (HSP) is an inherited disease characterized by lower extremity spasticity and weakness occurring in variable proportion.

About thirty heterozygous mutations in the DNM2 gene were identified as involved in AD-CNM, CMT, or HSP diseases, for which there is no available curative treatment.

Overexpression of DNM2 in absence of mutation is also involved in some pathophysiological mechanisms of other diseases such X-linked myotubular myopathy or cancers, for example prostate cancer and pancreatic cancer.

Therefore, there remains an urgent need for therapeutic compounds and methods for the treatment of diseases caused by heterozygous mutations and/or overexpression of DNM2.

Some research teams have developed strategies to inhibit Dynamin 2 using conventional siRNA or pharmacological inhibitors, in order to treat DNM2 overexpression-linked pathologies. The present invention relates to an improvement of these strategies which is able to inhibit mutated or overexpressed Dynamin 2, while preserving a sufficient amount of functional DNM2 allowing a normal cellular function.

SUMMARY OF THE INVENTION

In one aspect, the present invention provides an allele specific siRNA (AS-siRNA) able to silence the expression of only one allele of a heterozygous DNM2 gene in a cell. In a particular embodiment, the AS-siRNA of the invention is of 19-23 base pairs in length, preferably 19.

In a particular embodiment, the AS-siRNA of the invention is able to silence the expression of only one allele of a heterozygous DNM2 gene in a cell, the DNM2 gene being heterozygous for the presence of a non-pathological polymorphism, and/or being heterozygous for the presence of a disease-causing mutation.

In particular, the AS-siRNA of the invention targets a region of a DNM2 gene transcript comprising said non-pathological polymorphism. In a particular embodiment, said non-pathological polymorphism is on the same allele as the disease-causing mutation. More specifically, said non-pathological polymorphism is rs2229920 (C or T) or rs12461992 (A or T), preferably rs2229920 (C or T).

In a more particular embodiment, the AS-siRNA of the invention is of 19 base pairs in length and comprises a mismatch. This mismatch enables the AS-siRNA to specifically target and silence only the allele carrying said polymorphism, while preserving the other allele. In a particular embodiment, the position of the mismatch is located at position N16 or N17 from 5' end of the sense strand of said AS-siRNA, preferably at position N17.

In particular, the AS-siRNA comprises a sense strand selected in the group consisting of: SEQ ID NO:1, SEQ ID NO:2, SEQ ID NO:3 or SEQ ID NO:4, preferably SEQ ID NO:1 or SEQ ID NO:2.

In another particular embodiment, the AS-siRNA of the invention targets a region of a DNM2 gene transcript comprising said disease-causing mutation. More specifically, the disease-causing mutation is 1393C>T; c.1105C>T, c.1106G>A, c.1393C>T, c.1856C>T or c.1948G>A, preferably 1393C>T. In a particular embodiment, the AS-siRNA of the invention is of 19 base pairs in length and comprises a mismatch. This mismatch enables the AS-siRNA to specifically target and silence the mutant allele, while preserving the wild type allele. In a particular embodiment, the position of the mismatch is located at position N9, N10, N11, N12, N15 or N16 from 5' end of the sense strand of said AS-siRNA, preferably at position N9 or N10 and more preferably at position N9.

In particular, the AS-siRNA comprises a sense strand selected in the group consisting of: SEQ ID NO:5 to SEQ ID NO:10, preferably SEQ ID NO:5 or SEQ ID NO:6, and more preferably SEQ ID NO:5.

In some embodiments, the AS-siRNA of the invention is able to reduce expression of DNM2 mRNA and/or DNM2 protein by 20-60%, preferably around 50%.

Another aspect of the invention relates to a vector encoding the AS-siRNA of the invention, the vector being preferably a plasmid or a viral vector, such as an AAV vector.

The invention also relates to a target cell, which is transfected or transduced with the vector of the invention.

In a further aspect, the invention provides an in vitro method for silencing the expression of the mutated allele of DNM2 gene without silencing the expression of the wild type allele of the DNM2 gene in a target cell, comprising introducing in said target cell an AS-siRNA or a vector of the invention.

According to another aspect, herein is disclosed an AS-siRNA, a vector or a cell of the invention for use in a method for treating a disease associated with an overexpression of Dynamin 2, preferably for treating X-linked myotubular myopathy, or cancer such as prostate cancer and pancreatic cancer.

Another aspect of the invention relates to an AS-siRNA, a vector or a cell of the invention for use in a method for treating a disease induced by a disease-causing mutation(s) in the DNM2 gene, preferably for treating autosomal dominant centronuclear myopathy, T-cell acute lymphoblastic leukemia, Charcot-Marie-Tooth disease or Hereditary Spastic Paraplegia, and more preferably for treating autosomal dominant centronuclear myopathy.

Other aspects and embodiments of the invention will be apparent in the following detailed description.

LEGENDS OF THE FIGURES

FIG. 1. Screening for allele-specific siRNA in heterozygous Mouse Embryonic Fibroblasts (MEF). (A) Wild-type (WT; SEQ ID NO: 11) and mutated (R465W; SEQ ID NO: 12) mRNA sequences in the region of the nucleotide change are indicated as well as the sequences of the 19 possible siRNA targeting the single point mutation (siRNA sense strand which is not complementary to the mRNA sequence). Arrows show the 12 siRNA assessed in this study. (B) EcoNI digestion profile on agarose gel electrophoresis of the Dnm2 RT-PCR product centred on the mutated nucleotide. The siRNA are numbered relative to the position of the mismatch introduced between the siRNA and the WT sequences. Sc: Scramble siRNA. NT: non transfected cells. Histogram represents mean.+−.SEM of calculated HTZ/WT ratio for each siRNA. * P<0.05 using a Mann-Whitney U-test compared to Scramble value (n=5).

Figure 2:
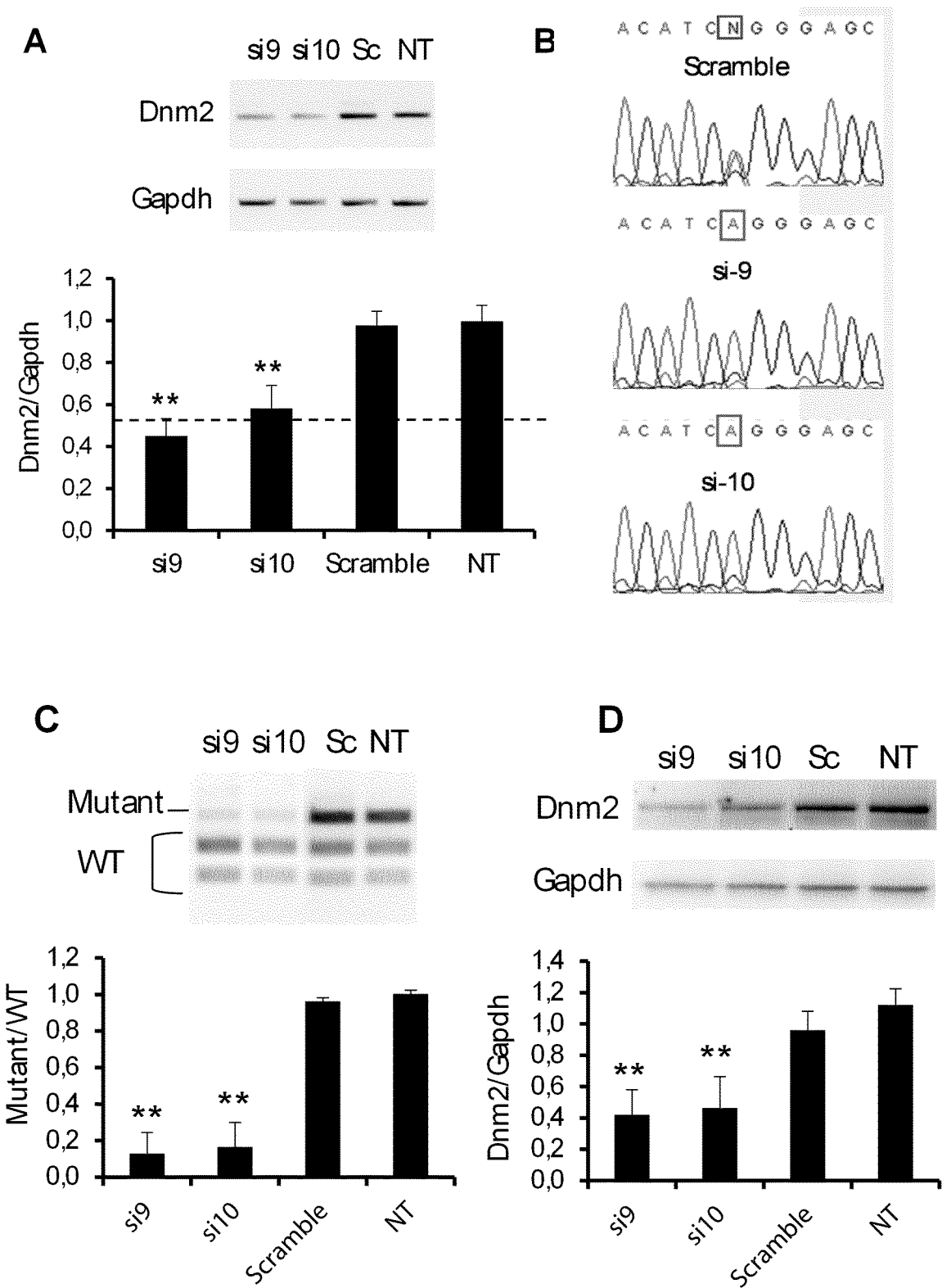

FIG. 2. Allele-specific si9 and si10 in heterozygous Mouse Embryonic Fibroblasts (MEF). (A) Agarose gel of RT-PCR products for Dnm2 and Gapdh mRNA and quantification of Dnm2 expression normalized to Gapdh used as a loading control. (B) Sequence of Dnm2 amplicons from cells transfected with si9, si10 and Scramble siRNA. Squares indicate the mutated nucleotide (N=T and A with Scramble siRNA) (C) EcoNI digestion profile of the Dnm2 amplicon on agarose gel electrophoresis and quantification of the Mutant/WT ratio. (D) Representative western blot against Dnm2 in treated and control cells and quantification of signal by densitometry. Gapdh was used as loading control. Sc: Scramble siRNA. NT: non transfected cells. In A, C, and D, histograms represent mean±SEM. ** P<0.001 using a Mann-Whitney U-test compared to Scramble values (n=5).

Figure 3:
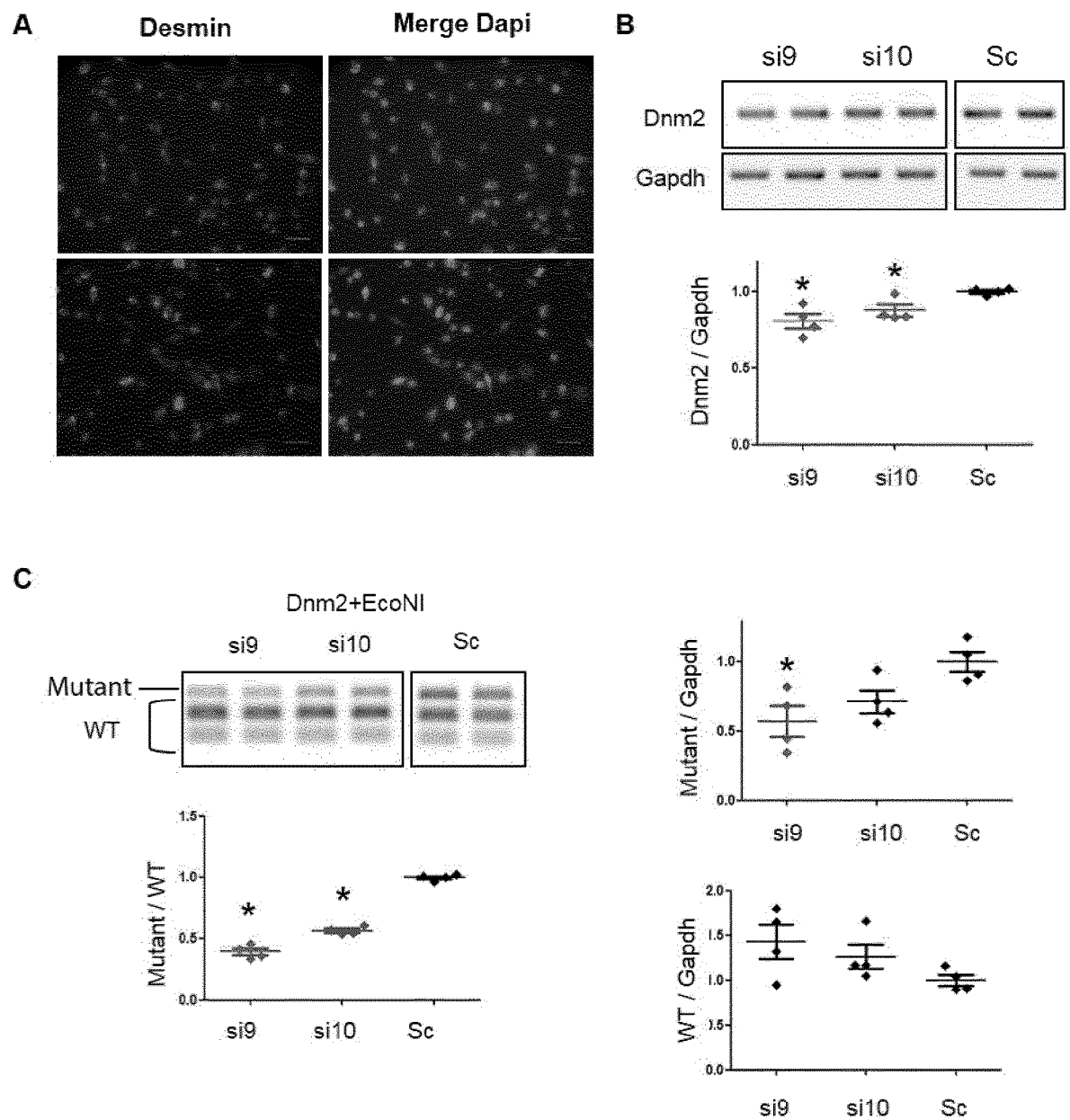

FIG. 3. si9 and si10 are allele-specific siRNAs in Mouse Myoblast. Cells were transfected with siRNAs at 100 nM for 48 h. (A) Representative images of Desmin immunostaining in immortalized mouse myoblast. Scale bars=50 μm. (B) Dnm2 and Gapdh semi-quantitative RT-PCR products from siRNA transfected myoblasts and quantification of Dnm2 expression normalized to Gapdh. (C) Quantification of the mutated and WT Dnm2 transcripts after RT-PCR and EcoNI digestion and normalization relative to Gapdh expression. Scatter plots bars represent mean±SEM. * P<0.05 using a one-tailed Mann-Whitney U-test compared to scramble values (n=4).

FIG. 4. Contractile properties in TA muscles. P0: absolute force. sP0: specific maximum tetanic force. mo: month. n: number of analyzed muscles. Statistical comparison was performed using a Mann-Whitney U-test. Statistical analysis vs WT: a: P<0.05 and b: P<0.001. Statistical analysis vs HTZ noSh: c: P<0.05, d: P<0.01 and e: P<0.001.

Figure 5:
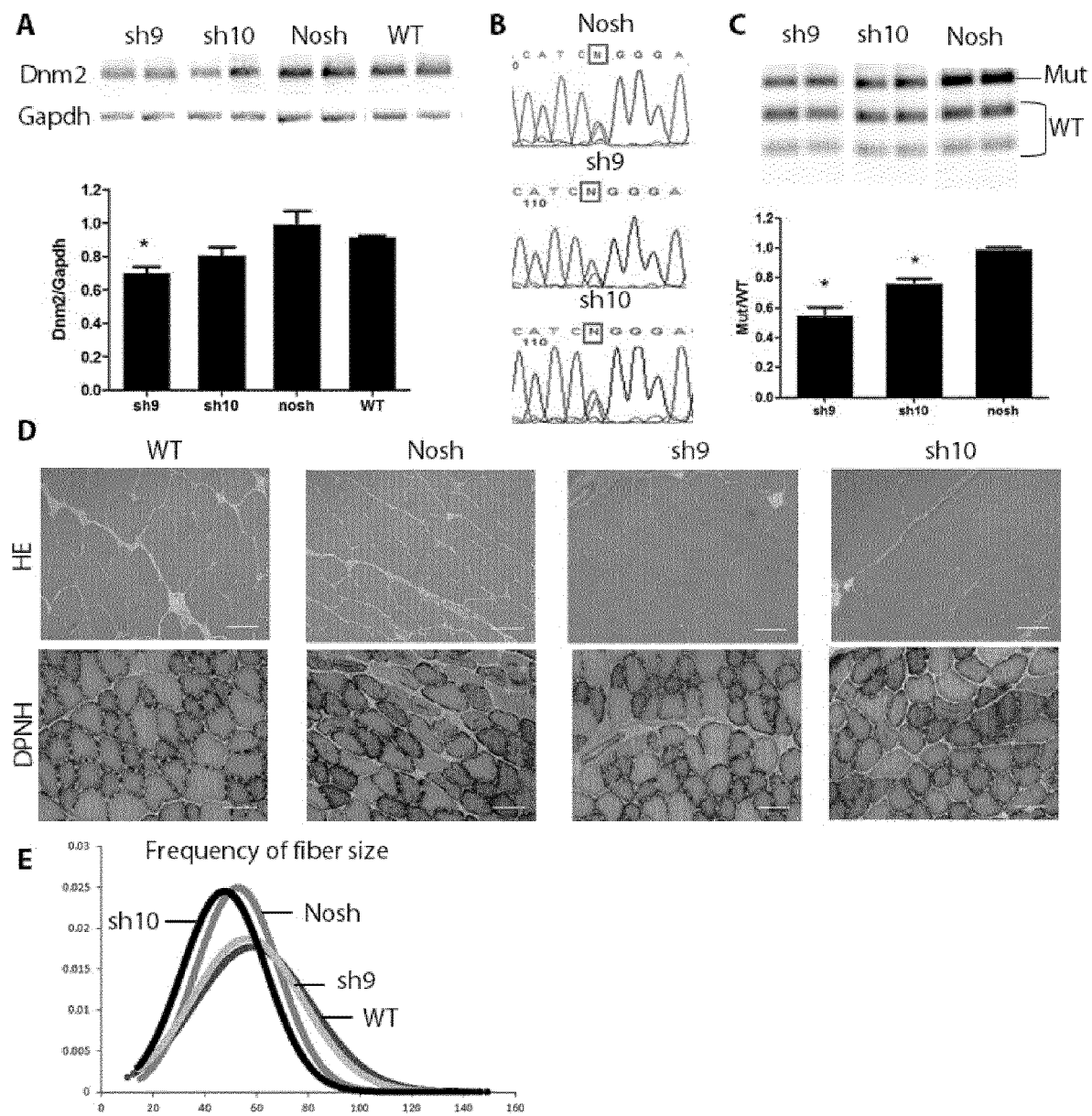

FIG. 5. Molecular and histological characterization of shAAV-transduced muscles in mice. (A) Agarose gel of RT-PCR products for Dnm2 and Gapdh mRNA from shAAV-transduced HTZ TA muscles and quantification of Dnm2 expression normalized to Gapdh used as a loading control. WT muscles were included as control. Histograms represent mean±SEM. * P<0.05 using a Mann-Whitney U-test compared to nosh value (n=5) (B) Sequence of Dnm2 amplicons from TA muscles transduced with sh9-, sh10- and nosh-AAV. Squares indicate position of the mutated nucleotide (N=T and A) (C) EcoNI digestion profile of the Dnm2 amplicon on agarose gel electrophoresis and quantification of the mutant/WT ratio. Histograms represent mean±SEM. * P<0.05 using a Mann-Whitney U-test compared to nosh value (n=5). (D) Representative histochemical staining of TA sections from WT and HTZ mice transduced with shAAV or empty AAV. HE: hematoxilin eosin staining. DPNH: Reduced diphosphopyridine nucleotide diaphorase staining. Scale bars=50 μm. (E) Quantification of the frequency of fibre size in transduced HTZ TA muscles. WT muscles were used as control (n=3 per condition).

Figure 6:
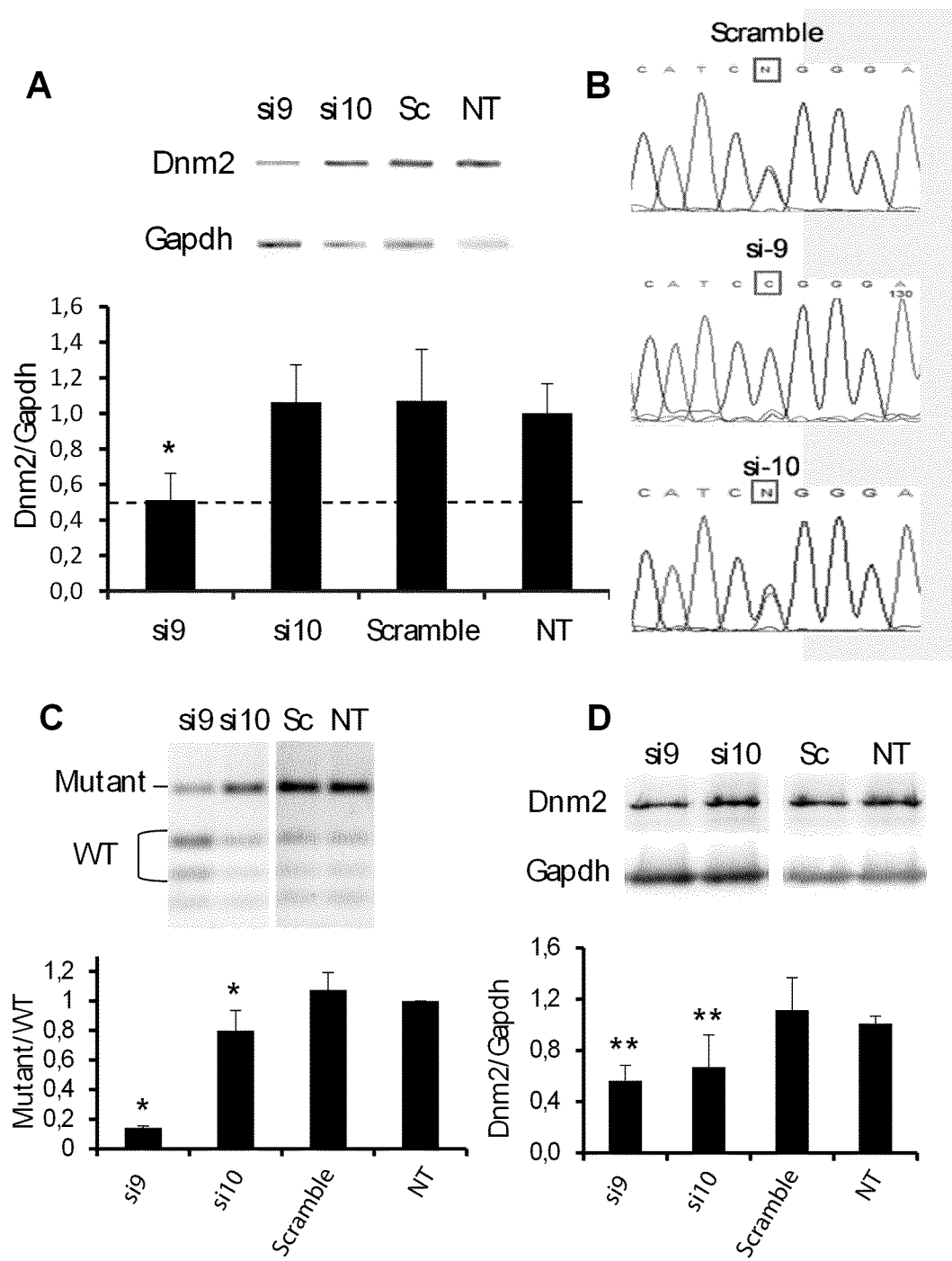

FIG. 6. Allele-specificity of si9 and si10 in patient-derived fibroblasts. (A) Agarose gel of RT-PCR products for Dnm2 and Gapdh mRNA and quantification of Dnm2 expression normalized to Gapdh used as a loading control. (B) Sequence of Dnm2 amplicons from cells transfected with si9, si10 and Scramble siRNA. Squares indicate the mutated nucleotide (N=T and C with Scramble and si10 siRNA) (C) PfoI digestion profile of the Dnm2 amplicon on agarose gel electrophoresis and quantification of the Mutant/WT ratio. (D) Representative western blot against Dnm2 in treated and control cells and quantification of signal by densitometry. Gapdh was used as loading control. Sc: Scramble siRNA. NT: non transfected cells. In A, C, and D, histograms represent mean±SEM. * P<0.05 and ** P<0.001 using a Mann-Whitney U-test compared to Scramble values (n=5).

Figure 7:
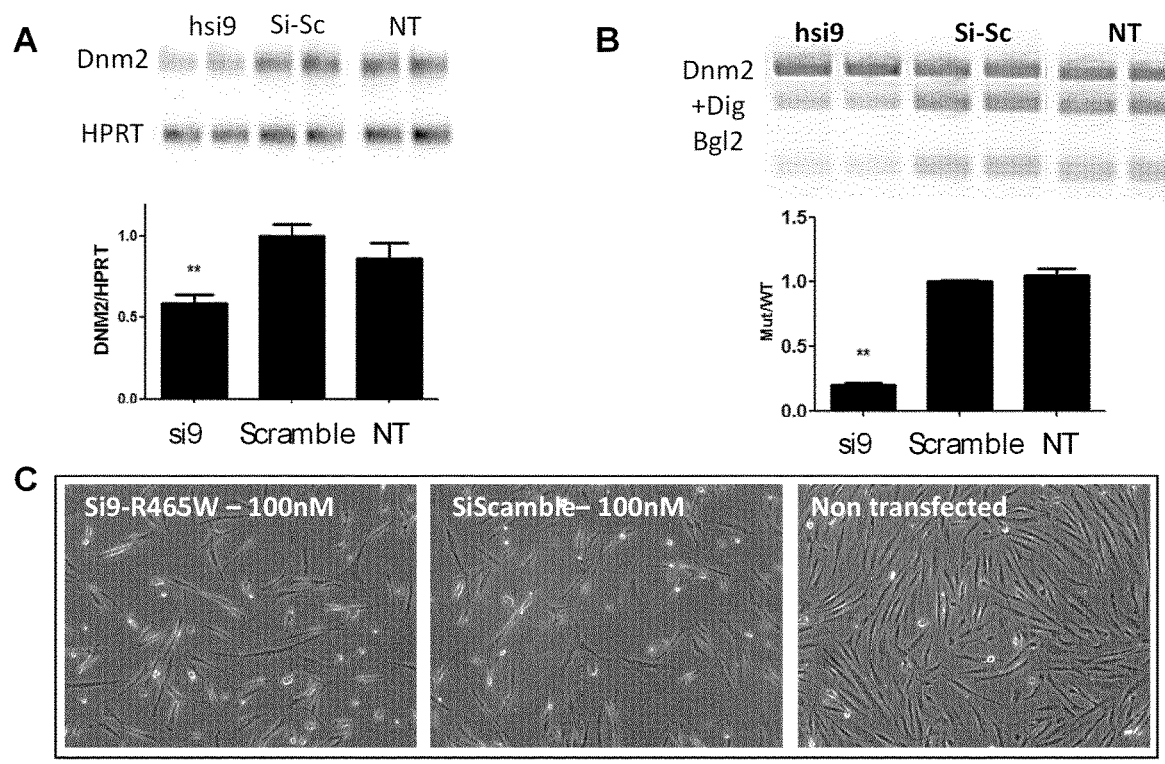

FIG. 7. Allele-specific silencing induced by si9 in human fibroblasts at 100 nM. (A) Agarose gel electrophoresis of Dnm2 and HPRT RT-PCR products 48 hours after transfection of siRNA at 100 nM. NT: non-transfected cells. Histogram represents mean±SEM of DNM2 normalized to HPRT.  P<0.001 using a Mann-Whitney U-test compared to scramble values (n=5). (B) BglI digestion profile of the DNM2 amplicon on agarose gel electrophoresis and quantification of the Mutant/WT ratio. Histogram represents mean±SEM.  P<0.001 using a Mann-Whitney U-test compared to scramble values (n=5). (C) Representative pictures of human fibroblasts 48 h after transfection with si9 and scramble siRNA at 100 nM.

Figure 8:
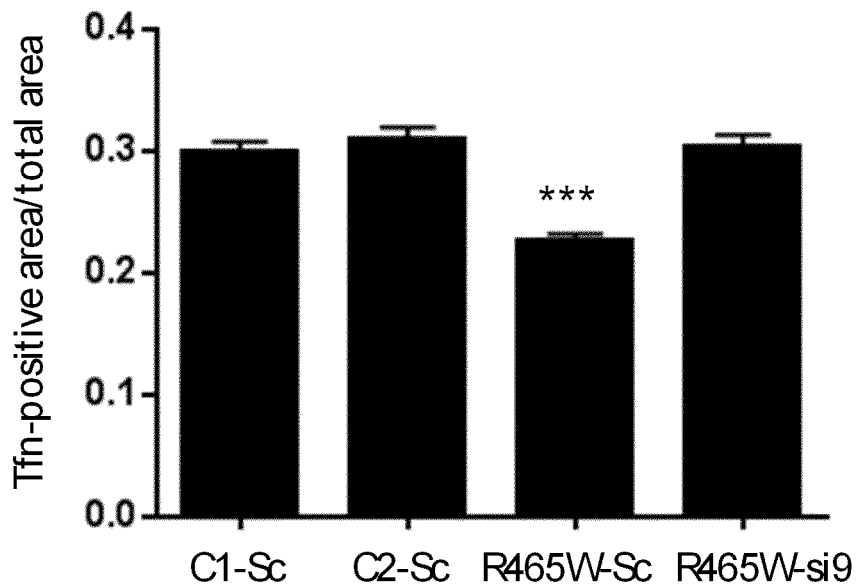
Figure 8:
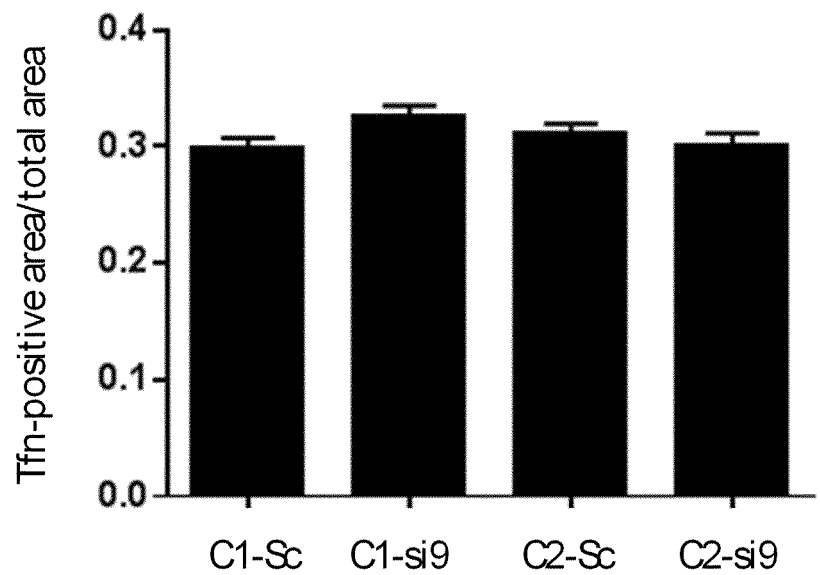

FIG. 8. Transferrin uptake assay in fibroblasts. (A) Transferrin uptake assay in patient-derived fibroblasts. Transferrin uptake was quantified after 15 min of incubation at 37° C. Histogram represents mean±SEM (n=65 cells from 2 independent experiments for each cell line) and statistical analysis was performed using a Student-t test (*** p<0.0001 versus the 2 control cell lines). (B) Transferrin uptake assay in healthy control fibroblasts. Transferrin uptake was quantified after 15 min of incubation at 37° C. Histogram represents mean±SEM (n=65 cells from 2 independent experiments for each cell line) and statistical analysis was performed using a Student-t test showing no significant difference between scramble and si9 values for each control cell line.

Figure 9:
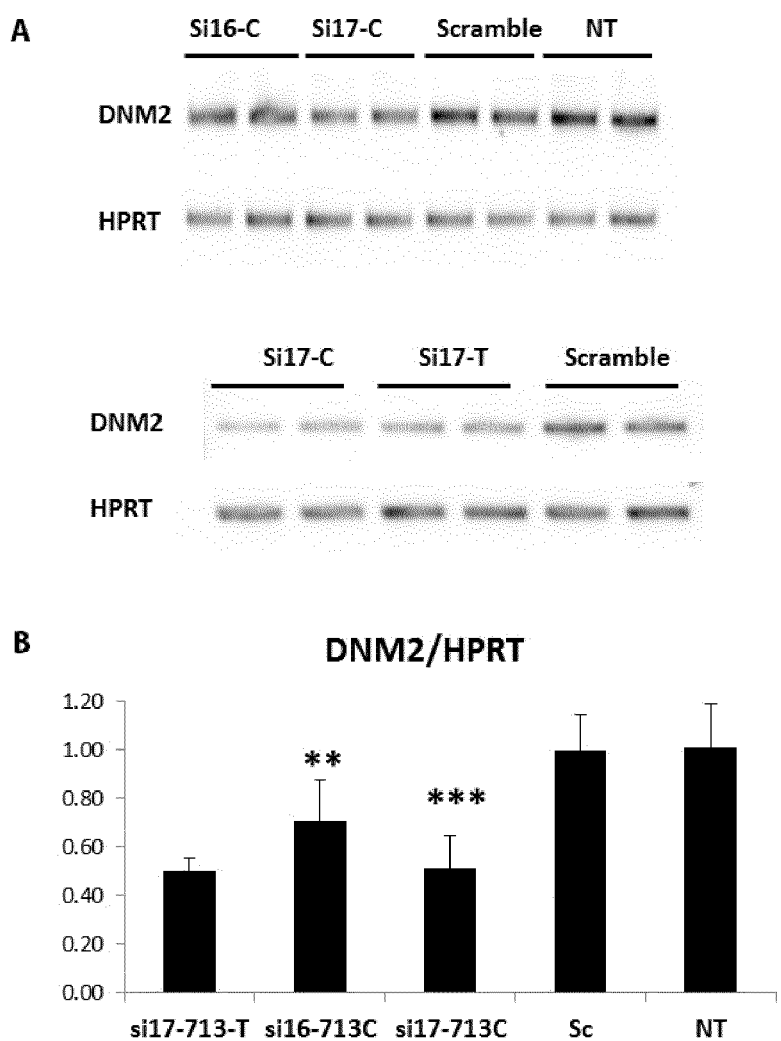

FIG. 9. Development of allele-specific siRNA against a non-pathogenic polymorphism in human cells. (A) Agarose gel of RT-PCR products for DNM2 and HPRT mRNA from human fibroblasts transfected by siRNA (30 nM for 48 hours) directed against the two versions of the heterozygous polymorphism (T or C). Scramble: Scramble siRNA. NT: non transfected cells. (B) Quantification of the DNM2/ HPRT ratio. Histogram represents mean±SEM.  P<0.01 and * P<0.0001 using a Mann-Whitney U-test compared to Scramble values (n=8 for NT, Scramble, si17-713C. n=6 for si16-713C. n=2 for si17-713T). Sc: Scramble siRNA.

Figure 10:
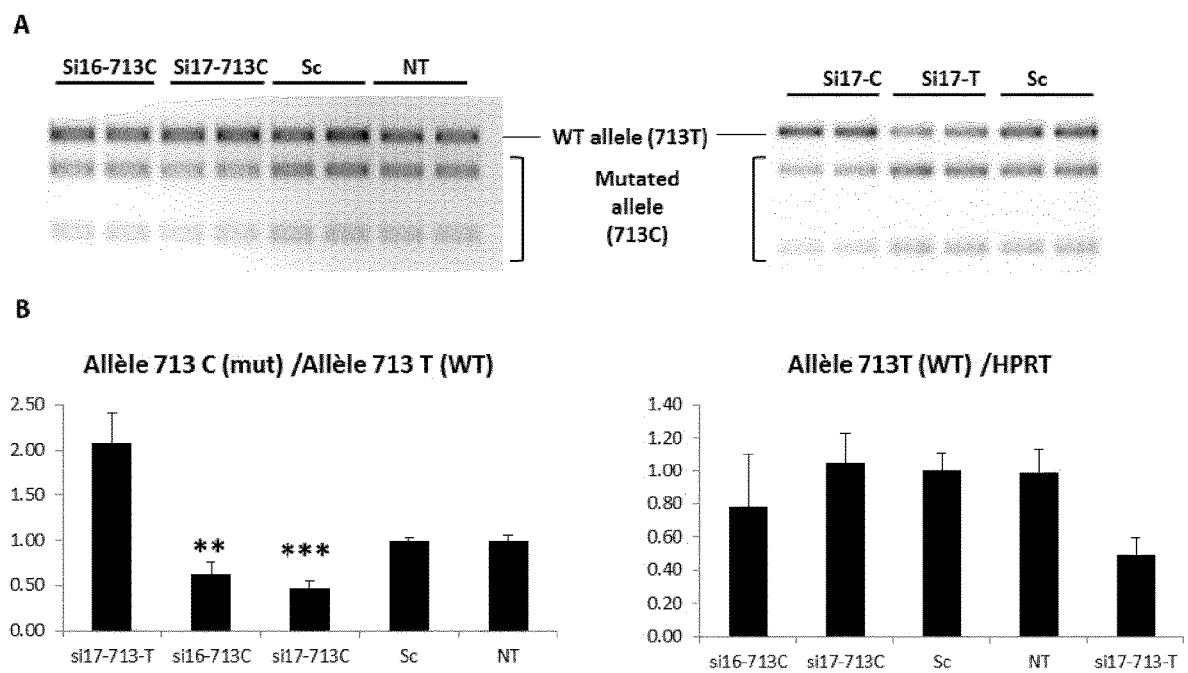

FIG. 10. Allele-specificity of siRNA against the heterozygous polymorphism. (A) Representative agarose gels of DNM2 RT-PCR products from cells transfected by siRNA (30 nM for 48 hours) or in non-transfected cells (NT). In this patient-derived cell line, the mutation is in frame with the version C of the polymorphism. The RT-PCR products are submitted to BglI digestion to discriminate between WT non-digested allele and mutated digested allele. (B) Quantification of the mutant/WT and WT/HPRT ratios. Histograms represent mean±SEM.  P<0.01 and * P<0.0001 using a Mann-Whitney U-test compared to Scramble values (n=8 for NT, Sc, si17-713C. n=6 for si16-713C. n=2 for si17-713T). Sc: Scramble siRNA. NT: non-transfected cells.

Figure 11:
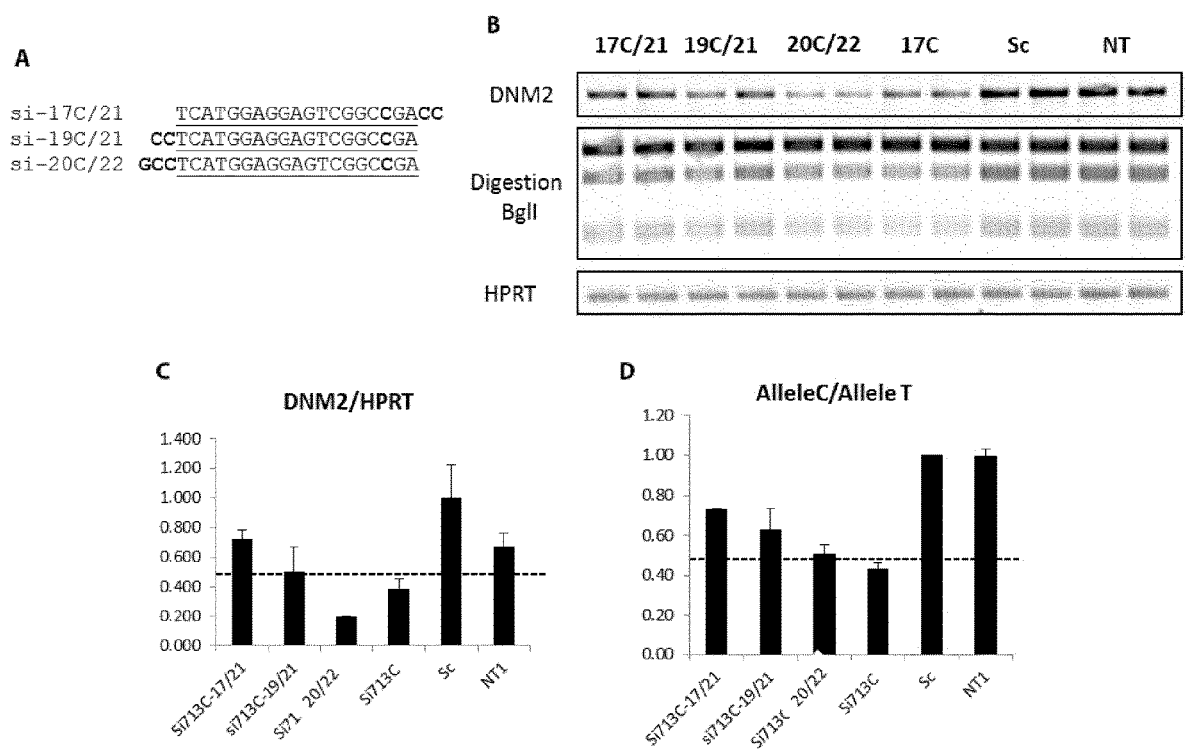

FIG. 11. Modification of the length of the allele-specific siRNA against the heterozygous polymorphism. (A) Sequence of the siRNA (si-17C/21 is SEQ ID NO: 34, si-19C/21 is SEQ ID NO: 36. and si-20C/22 is SEQ ID NO: 38). The underlined sequence shows the sequence of the 19-bp-length siRNA with the polymorphism (C in bold case) at the position 17. In bold are indicated the additional bases in the modified siRNA. (B) Agarose gel of total DNM2 RT-PCR products (top panel), RT-PCR products digested by BglI (middle panel) and HPRT RT-PCR product (bottom panel). (C) Quantification of the total DNM2/HPRT ratio. (D) Quantification of the allele C/allele T ratio. In C and D, Histograms represent mean.+−.SEM (n=2).

DETAILED DESCRIPTION OF THE INVENTION

The present disclosure is based on the unexpected discovery of allele specific siRNA (AS-siRNA) able to efficiently silence the expression of only one allele of a heterozygous DNM2 gene in a cell, said AS-siRNA being used for the treatment of DNM2-related diseases.

Dynamin 2 is encoded by the DNM2 gene (Gene ID 1785). More precisely, the DNM2 gene is located within the short arm of chromosome 19 at position 13.2 (19p13.2). The dynamin 2 gene or gene products are also known by other names, including but not limited to CMT2M, CMTDI1, CMTDIB, DI-CMTB, DYN2, DYN2 HUMAN, dynamin II, DYNII. DNM2 has an important role in endocytosis and in the cell's structural framework (cytoskeleton). The protein interacts with multiple parts of the cytoskeleton, including microtubules and actin, which organize into filaments to provide structure. These parts of the cytoskeleton are involved in movement of molecules within the cells, cell shape, cell mobility, and attachment of cells to one another or to extracellular matrix. An alteration in the DNM2 gene may thus disrupt endocytosis and interfere with the arrangement or dynamics of cytoskeletons leading to abnormal cellular function. As previously described, several dominant genetic diseases are caused by heterozygous mutations of the DNM2 gene such as autosomal dominant centronuclear myopathy, Charcot-Marie-Tooth disease and Hereditary Spastic Paraplegia. Overexpression of DNM2 is also pathological and involved in some pathophysiological mechanisms of other diseases such as X-linked myotubular myopathy or cancers, for example prostate cancer and pancreatic cancer.

The present inventors have investigated a therapeutic approach based on the specific suppression of the expression of only one allele of DNM2, preserving the other DNM2 allele. On one hand, this strategy aims to reduce in a controlled way the DNM2 expression level, in the case of diseases related to overexpression of DNM2. On the other hand, this strategy would be useful in autosomal dominant inherited diseases due to heterozygous mutation in the DNM2 gene, by specifically inhibiting the expression of a mutant allele without reducing the level of the wild type DNM2 allele which is required for a normal cellular function. With this objective, the present inventors discovered very efficient allele specific siRNAs able to inhibit, in a controlled way, only one allele of a heterozygous DNM2 gene in a cell.

A first aspect of the present invention is therefore an allele specific siRNA (AS-siRNA) able to silence the expression of only one allele of a heterozygous DNM2 gene in a cell.

RNA interference is a biological process in which RNA molecules inhibit gene expression, typically by causing the destruction of specific mRNA molecules. An interfering RNA is therefore an RNA which is capable of down-regulating the expression of the targeted protein. For example, it encompasses small interfering RNA (siRNA), double-stranded RNA (dsRNA), single-stranded RNA (ssRNA), and short hairpin RNA (shRNA) molecules. RNA interference designates a phenomenon by which dsRNA specifically suppresses expression of a target gene at post-transcriptional level. In normal conditions, RNA interference is initiated by double-stranded RNA molecules (dsRNA) of several thousands of base pair length. In vivo, a dsRNA introduced into a cell is cleaved by an enzyme called DICER into a mixture of short dsRNA molecules called siRNA. In mammalian cells, the siRNAs produced by Dicer are about 21 base-pairs (bp) in length. Then the siRNA join an RNase complex, RISC (RNA-induced silencing complex), which acts on the cognate mRNA and degrades it. RNA interference is also a valuable research tool, as double strand siRNA of 19 to 23 bp may be used to selectively and robustly induce suppression of specific genes of interest. The major interest of this approach is the specificity, as an siRNA is able to discriminate two sequences even when differing by only a single nucleotide.

The present inventors used said specificity of siRNA to specifically inhibit one allele of a heterozygous DNM2 gene. Consequently, in that particular case, the siRNA is called an "allele specific siRNA" (AS-siRNA).

By AS-siRNA is meant any siRNA able to specifically silence only one allele of a targeted gene, an allele being one of several alternative forms of a gene occupying a given locus on a chromosome. "Gene silencing" refers to the suppression or reduction of gene expression. Gene silencing may be mediated through processes that affect transcription and/or through processes that affect post-transcriptional mechanisms. In some embodiments, gene silencing occurs when siRNA initiates the degradation of the mRNA of the gene in a sequence-specific manner via RNA interference. Thus, a gene includes coding sequences and/or the regulatory sequences required for expression. For example, "gene" refers to a nucleic acid fragment that expresses mRNA, functional RNA, or specific protein, including regulatory sequences. "Genes" also include nonexpressed DNA segments that may, for example, form recognition sequences for other proteins.

In the context of the invention, the gene is the DNM2 gene, coding for Dynamin 2 protein. Thus, an AS-siRNA of the invention specifically silences one allele of the DNM2 gene, which is a variant form of the DNM2 gene.

In the context of the present invention, the DNM2 gene is a heterozygous DNM2 gene. A heterozygous DNM2 gene is a DNM2 gene present in a heterozygous state in a cell. By "heterozygous" is meant that a given chromosomal locus has two different alleles. Diploid organisms such as humans contain two copies of each chromosome (one maternal and one paternal chromosome), that are called homologous chromosomes. Therefore, each homologous chromosome carries one allele of a given gene. A diploid organism is heterozygous when said two alleles of a given gene are different in respect to a given variation or polymorphism.

In the context of the invention, a cell or an organism is heterozygous in respect to the DNM2 gene wherein the DNM2 gene is present in a heterozygous state, that is to say wherein the two alleles of DNM2 gene are different in respect to a given variation or polymorphism.

In one embodiment of the invention, heterozygous refers to a genotype in which one allele has a wild-type DNM2 sequence and the other allele has a sequence encoding a DNM2 variant. In particular, the sequence encoding a DNM2 variant comprises a mutation that is not present in the wild-type sequence.

In a first preferred embodiment, the DNM2 gene is heterozygous for the presence of a disease-causing mutation. In this embodiment, the AS-siRNA of the invention targets the allele of the DNM2 gene comprising said disease-causing mutation.

In a second preferred embodiment, the DNM2 gene is heterozygous for the presence of a non-pathological polymorphism. In this second embodiment, the AS-siRNA of the invention targets only one of the allele of the DNM2 gene, comprising or not said non-pathological polymorphism.

In what follows, those two preferred embodiments are separately described.

AS-siRNA Targeting the Allele of the DNM2 Gene Comprising a Disease-Causing Mutation DNM2 Gene Comprising a Disease-Causing Mutation In one embodiment of the invention, the DNM2 gene is heterozygous for the presence of a disease-causing mutation. Therefore, the DNM2 gene is present in two different forms corresponding to the two alleles: one DNM2 allele is a "wild type allele" whereas the other is a "mutant allele". In this embodiment, the AS-siRNA of the invention specifically targets and silences the allele of the DNM2 gene comprising said disease-causing mutation without targeting the wild type allele. The AS-siRNA is thus able to silence the expression of Dynamin 2 mRNA and Dynamin 2 protein derived from the mutant allele without affecting the expression of mRNA and protein derived from the wild type allele.

In particular, the disease-causing mutation could be any deletion, insertion or substitution of nucleotide(s) within the DNM2 gene which is responsible for a pathology or which is correlated to a pathology. In a preferred embodiment, the disease-causing mutation is a dominant mutation. By dominant mutation is meant any mutation that leads to a dominant allele. By "dominant allele" is meant an allele that exerts its effect on phenotype over the presence of a recessive allele of the same gene. The terms dominant and recessive alleles are defined relative to one another, and are not absolute. In other words, the phenotypic consequences of a dominant mutation are observed in a heterozygous individual carrying one mutant allele and one wild type allele. Recessive alleles only show their effect if the individual has two copies of the mutated allele (also known as being homozygous) or two different mutated alleles (also known as composite heterozygosity).

In a particular embodiment, the dominant mutation is a gain-of-function mutation. A gain-of-function mutation is defined as a mutation that confers new or enhanced activity on a protein. A gain-of-function mutation is a type of mutation in which the altered gene product possesses a new molecular function or a new pattern of gene expression. Consequently, the disease-causing mutation within the DNM2 leads to a gain-of-function of Dynamin 2 protein.

In a particular embodiment, the dominant mutation is a loss-of-function mutation by dominant negative effect. A loss-of-function mutation is defined as a mutation that results in the loss or reduction of the normal activity of a protein. Dominant-negative effect is defined as the product of a mutated allele alters the function of the product from the wild-type allele. This occurs, for example, when oligomerization is required for normal function on a protein and when the mutated protein is able to oligomerize with the wild-type protein. Consequently, the disease-causing mutation within the DNM2 leads to a loss-of-function of the wild-type Dynamin 2 protein due to the presence of the mutated Dynamin 2 protein.

In another particular embodiment, the DNM2 gene which is heterozygous for a disease-causing mutation is not haploinsufficient. Haploinsufficiency occurs when one copy of a gene is inactivated or deleted and the remaining functional copy of the gene is not adequate to produce sufficient amount of the gene product to preserve normal function. In other words, the wild type DNM2 allele of the invention is able to preserve normal function, following the silencing of the mutant allele by AS-siRNA of the invention. Therefore, the present invention preferably relates to autosomal dominant disease in which there is no haploinsufficiency.

In a particular embodiment, the dominant mutation within the DNM2 gene leads to an autosomal dominant disease. An autosomal dominant disease is a disease wherein the individual has one copy of a mutant gene and one normal gene on a pair of autosomal chromosomes (autosomal chromosome being any chromosome which is not a sex chromosome). An individual with autosomal dominant diseases has 50% chance of passing the mutant gene and therefore the disorder on to each of its children.

In one preferred embodiment, the autosomal dominant disease is selected from Autosomal Dominant Centronuclear Myopathy (AD-CNM), T-cell acute lymphoblastic leukemia, Charcot-Marie-Tooth disease (CMT) or Hereditary Spastic Paraplegia (HSP). Preferably, the autosomal dominant disease is Autosomal Dominant Centronuclear Myopathy (AD-CNM).

In another embodiment, the disease-causing mutation within the DNM2 gene is responsible for or correlated to a disease selected from Autosomal Dominant Centronuclear Myopathy (AD-CNM), T-cell acute lymphoblastic leukemia, Charcot-Marie-Tooth disease (CMT) or Hereditary Spastic Paraplegia (HSP). Preferably, the disease-causing mutation within the DNM2 gene is responsible for or correlated to Autosomal Dominant Centronuclear Myopathy (AD-CNM).

In a preferred embodiment, the disease-causing mutation within the DNM2 gene is a substitution of a single nucleotide, more preferably the disease-causing mutation is a missense mutation. By missense mutation is meant a point mutation in which a single nucleotide change results in a codon coding for a different amino acid. In a particular embodiment, the target allele encodes a protein with at least one mutation associated to AD-CNM selected in the group consisting of: p.E368K, p.E368Q, p.R369W, p.R369Q, p.V375G, p.R465W, p.R522H, p.R522C, p.R523G, p.E540K, p.E560K, p.D614N, p.A618T, p.A618D, p.S619L, p.S619W, p.L621P, p.624ins-1G, p.V625del, p.P627H, p.P627R, p.KDQ629-631del-ins, p.P647R and p.E650K or with at least one mutation associated to CMT selected in the group consisting of p.G358R, p.G537C, p.K554fs, p.D555_E557del, p.K559del, p.K562E, p.K562del, p.L570H, p.M580T, and p.859-860del. For these two groups of mutations, amino-acids are numbered relative to the human DNM2 isoform 1 (NP_001005360.1). In a more preferred embodiment, the DNM2 gene is heterozygous for the presence of a missense mutation selected in the group consisting of: c.1393C>T; c.1105C>T; c.1106G>A; c.1393C>T; c.1856C>T or c.1948G>A, respectively responsible for the following substitution in the DNM2 protein sequence: p.R465W, p.R369W, p.R369Q, p.R522H, p.S619L, and p.E650K. In an even more preferred embodiment, the DNM2 gene is heterozygous for the presence of the c.1393C>T mutation, responsible for the p.R465W substitution in the DNM2 protein sequence.

AS-siRNA

The AS-siRNA of the invention is able to silence the mutant allele of DNM2 gene, by hybridizing specifically to the gene transcript (messenger RNA or mRNA) derived from said mutant allele of DNM2 gene. The AS-siRNA of the invention is therefore complementary to a mRNA derived from said mutant allele of DNM2 and binds to said mRNA by base pairing. The term "complementary" refers to the ability of polynucleotides to form base pairs with another polynucleotide molecule. Base pairs are typically formed by hydrogen bonds between nucleotide units in antiparallel polynucleotide strands. Preferably, the degree of complementarity between the AS-siRNA according to the invention and the target mRNA is equal to about 100%.

In a particular embodiment, the AS-siRNA of the invention targets a region of the DNM2 gene transcript comprising said disease-causing mutation. Accordingly, the AS-siRNA of the invention is complementary to a sequence of the mRNA comprising said disease-causing mutation. The specificity of siRNA allows discriminating two sequences, even when differing by a single nucleotide. This property allows the AS-siRNA of the invention targeting disease-causing mutations, such as mutations resulting to single nucleotide substitution.

In one embodiment of the invention, the AS-siRNA is of 19-23 base pairs in length, such as 19, 20, 21, 22 or 23. In a preferred particular embodiment, the AS-siRNA of the invention is of 19 base pairs in length.

In a particular embodiment, the AS-siRNA of the invention contains nucleotide overhangs on 3' end of each strand. In a more particular embodiment, the AS-siRNA of the invention contains dinucleotide overhangs made of two deoxythymidines (dTdT) on 3' end of each strand.

In some embodiments, AS-siRNA of the invention is fully complementary to the mutant DNM2 mRNA sequence comprising said disease-causing mutation (encoded by the mutant allele). On the other hand, the AS-siRNA of the invention is complementary to the wild type DNM2 mRNA sequence (encoded by the wild type allele), except for a single nucleotide mismatch, at a position wherein the nucleotide is not mutated, when compared to the mutant mRNA. This mismatch enables the AS-siRNA to specifically target and silence the mutant allele, while preserving the wild type allele.

In a particular embodiment, the DNM2 gene is heterozygous for the presence of the c.1393C>T mutation, responsible for the p.R465W substitution in the DNM2 protein sequence, and the AS-siRNA of the invention is of 19 base pairs in length. Accordingly, the position of said mismatch could be in any of the 19 possible positions within the AS-siRNA.

In a preferred embodiment, the position of the mismatch is located at position N9, N10, N11, N12, N15 or N16 from 5' end of the sense strand of AS-siRNA. More preferably, the position of the mismatch is located at position N9 or N10, and even more preferably at position N9. By "sense strand" is meant the strand of the AS-siRNA which has the same sequence as the targeted mutant allele comprising said disease-causing mutation. Therefore, the other strand of AS-siRNA is called "anti-sense" because its sequence is complementary to the targeted mutant DNM2 mRNA, which is called the "sense" sequence (so that a sense segment of mRNA "5'-AAGGUC-3'" would be hybridized by the anti-sense mRNA segment "3'-UUCCAG-5'").

By "position N9 from 5' end of the sense strand" is meant the ninth nucleotide from the 5' end of the sense strand (which has the same sequence as the target sequence). Position N9 from 5' end of the sense strand corresponds to position N11 from the 5' of the antisense strand, when the siRNA is of 19 base pairs in length.

In a particular embodiment, the invention relates to an AS-siRNA of 19-23 base pairs in length wherein the sense strand comprises a sequence selected from the group consisting of: SEQ ID NO:5 to SEQ ID NO:10, preferably SEQ ID NO:5 or SEQ ID NO:6, and more preferably SEQ ID NO:5.

In a more particular embodiment, the invention relates to an AS-siRNA of 19-23 base pairs in length wherein the sense strand consists in a sequence selected from the group consisting of: SEQ ID NO:5 to SEQ ID NO:10, preferably SEQ ID NO:5 or SEQ ID NO:6, and more preferably SEQ ID NO:5.

In a particular embodiment, the AS-siRNA of the invention is used to reduce expression of total DNM2 mRNA and/or DNM2 protein by 20-60%, such as 20, 30, 40, 50 or 60%. Preferably, the AS-siRNA of the invention is used to reduce expression of total DNM2 mRNA and/or DNM2 protein by about 50%. By «about» is meant a value of + or −10%, preferably + or −5%. For example, about 50% means from 45 to 55%, preferably from 47.5 to 52.5%.

As-siRNA Targeting the Allele of DNM2 Gene Comprising a Non-Pathological Polymorphism DNM2 Gene Comprising a Non-Pathological Polymorphism Another aspect of the invention relates to an AS-siRNA able to silence the expression of only one allele of a heterozygous DNM2 gene in a cell, wherein the DNM2 gene is heterozygous for the presence of a non-pathological polymorphism.

In a particular embodiment, the DNM2 gene comprises a common heterozygous non-pathological polymorphism. "Common heterozygous non pathological polymorphism" refers to a polymorphism with high heterozygous frequency that is to say that is frequent in the population at heterozygous state. By "frequent" is meant a polymorphism which is found at heterozygous state in at least 20%, 30%, 40% of general population, preferably at least 40%.

By "non-pathological polymorphism" is meant a variation in the nucleic acid sequence of a gene that is not associated with a disease. As such, according to the present invention, a non-pathological polymorphism corresponds to a sequence variation in a gene that, when considered independently of other sequence modifications, is not by itself associated to a pathology. For the sake of clarity, if a non-pathological polymorphism is heterozygous in a cell, it means that both polymorphisms are considered non-pathological, if considered independently of other sequence variations that might occur on the same gene. Non-pathological polymorphisms may include variations in coding and non-coding regions. Furthermore, non-pathological polymorphisms include nucleotide substitutions, deletions, and/or additions, including those that result in missense and nonsense mutations which do not lead to a pathology. Preferably, the non-pathological polymorphism is a single nucleotide substitution.

By targeting heterozygous common polymorphisms, the AS-siRNA of the invention can be used to reduce the expression of DNM2 protein, especially when overexpression of DNM2 in absence of mutation is associated with a pathological condition. For example, overexpression of DNM2 protein, in absence of mutation is correlated to X-linked myotubular myopathy or cancer such as prostate cancer and pancreatic cancer. Thus, the invention relates to an AS-siRNA wherein the AS-siRNA targets a DNM2 allele comprising a non-pathological polymorphism.

In another embodiment, the DNM2 allele comprising a non-pathological polymorphism is on the same allele as a heterozygous disease-causing mutation. By targeting heterozygous common polymorphisms rather than each specific disease-causing mutation, a single AS-siRNA can be used to inhibit expression of more than one disease-causing mutation in more than one patient. Accordingly, in one embodiment, the targeted version of the heterozygous non-pathological polymorphism is present on the same allele as said disease-causing mutation and is absent on the wild type allele which harbors the other version of the polymorphism. In other words, targeting a heterozygous non-pathological polymorphism allows differentiating mutant and wild-type DNM2 alleles. Said disease-causing mutation can be any heterozygous mutation within the DNM2 gene responsible for or associated to a disease. For example, the disease-causing mutation within the DNM2 gene is responsible for or correlated to a disease selected from Autosomal Dominant Centronuclear Myopathy (AD-CNM), T-cell acute lymphoblastic leukemia, Charcot-Marie-Tooth disease (CMT) or Hereditary Spastic Paraplegia (HSP). Preferably, the disease-causing mutation within the DNM2 gene is responsible for or correlated to Autosomal Dominant Centronuclear Myopathy (AD-CNM). In a more preferred embodiment, the DNM2 gene is heterozygous for the presence of a missense mutation selected in the group consisting of: c.1393C>T; c.1105C>T; c.1106G>A; c.1393C>T; c.1856C>T or c.1948G>A, respectively responsible for the following substitution in the DNM2 protein sequence: p.R465W, p.R369W, p.R369Q, p.R522H, p.S619L, and p.E650K. In an even more preferred embodiment, the DNM2 gene is heterozygous for the presence of the c.1393C>T mutation, responsible for the p.R465W substitution in the DNM2 protein sequence.

In a particular embodiment, the heterozygous non-pathological polymorphism is rs2229920 (C or T) or rs12461992 (A or T), preferably rs2229920 (C or T).

AS-siRNA

The AS-siRNA of the invention is able to silence only one allele of DNM2 gene comprising a heterozygous non-pathological polymorphism, by hybridizing specifically to the gene transcript (messenger RNA or mRNA) derived from said allele of DNM2 gene. AS-siRNA of the invention is therefore complementary to mRNA derived from said allele of DNM2 and binds to said mRNA by base pairing. The term "complementary" refers to the ability of polynucleotides to form base pairs with another polynucleotide molecule. Base pairs are typically formed by hydrogen bonds between nucleotide units in antiparallel polynucleotide strands. Preferably, the degree of complementarity between the AS-siRNA according to the invention and the target mRNA is equal to about 100%.

In a particular embodiment, AS-siRNA of the invention targets a region of the DNM2 gene transcript comprising said non-pathological polymorphism. Accordingly, the AS-siRNA of the invention is complementary to a sequence of the mRNA comprising said non-pathological polymorphism. The specificity of siRNA allows discriminating two sequences, even when differing by a single nucleotide. This property allows the AS-siRNA of the invention targeting polymorphism resulting to single nucleotide substitution.

In one particular embodiment, the target allele (and consequently the target mRNA) could be arbitrarily chosen, in absence of disease-causing mutation, in order to reduce the level of DNM2 mRNA and/or protein. In particular, the AS-siRNA of the invention could target the mRNA carrying or not said non-pathological polymorphism, when the goal is only to reduce the overall level of DNM2 mRNA or DNM2 protein. For example, the AS-siRNA of the invention could target anyone of the DNM2 allele carrying one of the two version of the heterozygous non-pathological polymorphism, wherein DNM2 is overexpressed in a cell, for example in X-linked myotubular myopathy or cancer such as prostate cancer and pancreatic cancer.

In another particular embodiment, the targeted version of the non-pathological polymorphism is present on the same allele as a disease-causing mutation. Therefore, the AS-siRNA of the invention targets and silences only the allele carrying said targeted version of the polymorphism and said disease-causing mutation. This particular embodiment requires prior confirming the location of the disease-causing mutation.

In one embodiment of the invention, the AS-siRNA is of 19-23 base pairs in length, such as 19, 20, 21, 22 or 23. In a preferred particular embodiment, the AS-siRNA of the invention is of 19 base pairs in length.

In a particular embodiment, the AS-siRNA of the invention contains nucleotide overhangs on 3' end of each strand. In a more particular embodiment, the AS-siRNA of the invention contains dinucleotide overhangs made of two deoxythymidines (dTdT) on 3' end of each strand.

In some embodiments, the AS-siRNA of the invention is fully complementary to the DNM2 mRNA sequence comprising said targeted version of non-pathological polymorphism. On the other hand, the AS-siRNA of the invention is complementary to the DNM2 mRNA sequence that does not comprise said polymorphism (encoded by the other allele), except for one single nucleotide mismatch, at a position wherein the polymorphism is absent. This mismatch enables the AS-siRNA to specifically target and silence only the allele carrying said polymorphism, while preserving the other allele.

In a particular embodiment, the DNM2 gene is heterozygous for the presence of the non-pathological polymorphism rs2229920 (C or T), which is found in 40% of individuals at heterozygous state. Therefore, the invention relates to an AS-siRNA that targets either the sequence comprising a C or the sequence comprising a T (corresponding to U in mRNA sequence).

In a preferred embodiment, the AS-siRNA of the invention targets the non-pathological polymorphism rs2229920 (C or T) and is of 19 base pairs in length. Accordingly, the position of the said mismatch could be in any of the 19 possible positions within the AS-siRNA.

In a preferred embodiment, the position of the mismatch is located at position N16 or N17 from 5' end of the sense strand of AS-siRNA. More preferably, the position of the mismatch is located at position N17. By "sense strand" is meant the strand of the AS-siRNA which has the same sequence as the targeted allele comprising said non-pathological polymorphism. Therefore, the other strand of AS-siRNA is called "anti-sense" because its sequence is complementary to the targeted DNM2 mRNA, which is called the "sense" sequence (so that a sense segment of mRNA "5'-AAGGUC-3'" would be blocked by the anti-sense mRNA segment "3'-UUCCAG-5'").

By "position N17 from 5' end of the sense strand" is meant the seventeenth nucleotide from the 5' end of the sense strand (which has the same sequence as the target sequence). Position N17 from 5' end of the sense strand corresponds to position N3 from the 3' of the antisense strand, wherein the siRNA is of 19 base pairs in length.

In a particular embodiment, the invention relates to an AS-siRNA of 19-23 base pairs in length, wherein the sense strand comprises a sequence selected from the group consisting of: SEQ ID NO:1 to SEQ ID NO:4, preferably SEQ ID NO:1 or SEQ ID NO:2.

In a more particular embodiment, the invention relates to an AS-siRNA of 19-23 base pairs in length, wherein the sense strand consists of a sequence selected from the group consisting of: SEQ ID NO:1 to SEQ ID NO:4, preferably SEQ ID NO:1 or SEQ ID NO:2.

In a particular embodiment, the AS-siRNA of the invention is used to reduce expression of DNM2 mRNA and/or DNM2 protein by 20-60%, such as 20, 30, 40, 50 or 60%. Preferably, the AS-siRNA of the invention is used to reduce expression of DNM2 mRNA and/or DNM2 protein by about 50%. By «about» is meant a value of + or −10%, preferably + or −5%. For example, about 50% means from 45 to 55%, preferably from 47.5 to 52.5%.

Methods and Uses of AS-siRNA

The present invention contemplates various ways of reaching the target mRNA with AS-siRNA of the invention. The AS-siRNA may be administered to the cell as isolated oligonucleotide, either directly or using transfection reagents such as lipidic derivatives, liposomes, calcium phosphate, nanoparticles, microinjection or electroporation.

In another embodiment, the present invention contemplates introducing the AS-siRNA into the cell in the form of a vector. Thus, another aspect of the present invention relates to a vector encoding the AS-siRNA of the invention. The vector may in particular be a plasmid or a viral vector. Representative viral vectors useful in the practice of the invention include, without limitation, a vector derived from adenovirus, retrovirus, in particular lentivirus, poxviruses, herpes simplex virus I and adeno-associated virus (AAV). In a particular embodiment, the vector is an AAV1, AAV8 or AAV9 vector. Selection of the appropriate viral vector will of course depend on the targeted cell and the virus tropism. In a particular embodiment, targeted cells are muscle cells, but viral vectors with broad tropism, including in particular the muscle tropism, may also be implemented. In a particular embodiment, an AAV1 vector is implemented, for example for use in intramuscular injections. In another embodiment, the vector is to be administered via the systemic route (for example via the intravascular or intraarterial route), and the vector is an AAV8 or AAV9 vector.

In a particular embodiment, the invention also relates to shRNA (short hairpin RNA) corresponding to the AS-siRNA of the invention, with a further tight hairpin turn. The shRNA hairpin structure is then cleaved by the cellular machinery into siRNA. A further aspect of the invention relates to a vector encoding shRNA corresponding to AS-siRNA of the invention. In another aspect, the invention also relates to a target cell comprising an AS-siRNA of the invention or which is transfected or transduced with a vector of the invention. For example, the target cell may be selected from: a muscle cell (or a cell of the muscle lineage), such as myoblast, for example a patient-derived myoblast, or a fibroblast such as a patient-derived fibroblast.

In another aspect, the present invention relates to an in vitro method for silencing the expression of the mutated allele of DNM2 gene without silencing the expression of the wild type allele of the DNM2 gene in a target cell, such as a muscle target cell (for example a muscle cell, such as a myoblast, in particular a patient-derived myoblast), comprising introducing in said target cell an AS-siRNA or a vector of the invention.

In another aspect, the present invention relates to an in vitro method for silencing the expression of one allele of DNM2 gene carrying a heterozygous non-pathological polymorphism without silencing the expression of the other allele of the DNM2 gene in a target cell, comprising introducing in said target cell an AS-siRNA or a vector of the invention.

In a further aspect, the present invention relates to an AS-siRNA, a vector or a cell of the invention for use in a method for treating a disease induced by a disease-causing mutation in the DNM2 gene. Preferably, an AS-siRNA, a vector or a cell of the invention are used in a method for treating centronuclear myopathy (such as autosomal dominant centronuclear myopathy), T-cell acute lymphoblastic leukemia, Charcot-Marie-Tooth disease (CMT) or Hereditary Spastic Paraplegia (HSP). More preferably, an AS-siRNA, a vector or a cell of the invention are used in a method for treating autosomal dominant centronuclear myopathy.

In another aspect, the present invention relates to an AS-siRNA, a vector or a cell of the invention for use in a method for treating a muscular dystrophy such as Duchenne muscular dystrophy.

In another aspect, the present invention relates to an AS-siRNA, a vector or a cell of the invention for use in a method for treating a disease associated with overexpression of dynamin 2, preferably for treating X-linked myotubular myopathy, or cancer such as prostate cancer and pancreatic cancer.

As used herein, the term "treating" and "treatment" refers to administering to a subject an effective amount of an AS-siRNA of the invention so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Alternatively, treatment is "effective" if the progression of a disease is reduced or halted. "Treatment" can also mean prolonging survival as compared to expected survival if not receiving treatment. Those in need of treatment include those already diagnosed with a DNM2 associated disorder, as well as those likely to develop such a disorder due to genetic susceptibility or other factors. As used herein, the term "treating" and "treatment" also refers the prevention of a disease or disorder, which means delaying or preventing the onset of such disease or disorder.

The AS-siRNA of the invention, the vector or the cell according to the invention can be formulated and administered to treat any disease caused by a heterozygous mutation in the DNM2 gene or caused by overexpression of DNM2, preferably to treat autosomal dominant centronuclear myopathy, T-cell acute lymphoblastic leukemia, Charcot-Marie-Tooth disease, Hereditary Spastic Paraplegia, X-linked myotubular myopathy, or cancer such as prostate cancer and pancreatic cancer. AS-siRNA of the invention, the vector or the cell according to the invention are formulated by any means that produces contact of the AS-siRNA with its site of action in the subject in need thereof.

The present invention also provides pharmaceutical compositions comprising the AS-siRNA of the invention, the vector or the cell according to the invention. Such compositions comprise a therapeutically effective amount of the therapeutic (the AS-siRNA, vector or cell of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as saline solution, water and oils, including those of petroleum, animal, vegetable or synthetic origin, such as peanut oil, soybean oil, mineral oil, sesame oil and the like. Physiological saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject.

The pharmaceutical composition is adapted for any type of administration to a mammal, in particular a human being and is formulated in accordance with routine procedures. The composition is formulated by using suitable conventional pharmaceutical carrier, diluent and/or excipient. Administration of the composition may be via any common route so long as the target tissue is available via that route.

The amount of the therapeutic of the invention which will be effective in the treatment of a nucleotide repeat expansion can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the AS-siRNA, the vector or the cell administered to the subject in need thereof will vary based on several factors including, without limitation, the route of administration, the subject's age or the level of expression necessary to obtain the required therapeutic effect. One skilled in the art can readily determine, based on its knowledge in this field, the dosage range required based on these factors and others.

EXAMPLES

AS-siRNA Targeting the Allele of the DNM2 Gene Comprising a Disease-Causing Mutation Materials and Methods Cell Cultures Mouse Embryonic Fibroblasts (MEF) were prepared from 13.5 day-old embryos. Cells were cultured at 37° C. (5% CO2) in Dulbecco's modified Eagle's medium (DMEM) containing 10% foetal calf serum (FCS) supplemented with penicillin, streptomycin, L-glutamate, and sodium pyruvate. Experiments were performed on MEFs in primary cultures, i.e. 2 or 3 passages after embryo dissection. Human skin fibroblasts from healthy control subjects (C1 and C2) and from one DNM2-linked CNM patient harbouring the p.R465W mutation were cultured using the same medium. Experiments were performed on immortalized cell population after transduction with lentivirus expressing human telomerase reverse transcriptase (hTERT). For transfection, cells were grown to 70% confluency and transfected with siRNA using JetPrime transfection reagent according to the manufacturer's protocol (Polyplus Transfection, France). Concentration of siRNA for each experiment are indicated in figure legend. Scramble siRNA (Eurogentec, Belgium) was used as control. Cells were harvested 48 h later for RNA and protein extraction or immunohistochemistry.

Total RNA Extraction and cDNA Analysis

Total RNA was isolated using RNA easy or RNA easy Fibrous tissue mini kits (Qiagen, France) for cells and muscles, respectively, according to the manufacturer's protocol. Cells or tissue sections were passed through a 22G syringe several times for disruption in the lysis buffer. Total RNA (1 µg) was submitted to reverse transcription using the Superscript III reverse transcriptase kit (Life Technologies) using hexamer primers. cDNA were amplified by PCR under the following conditions: 96° C. for 5 min, cycles of 30 s at 96° C., 30 s at the appropriate temperature (58 to 62° C.), 30 s to 1 min at 72° C., and a final step of 7 min at 72° C. Twenty three cycles were performed to amplify Gapdh, 28 for semi-quantitative analysis of Dnm2, 30 for restriction enzyme digestion of the human and murine Dnm2 amplicons, and 30 for genotyping and for the other PCRs. Sequences of all the primers used are indicated in the following table:

Table: Primers used in this study

| Target | | Sequence (5'-3') | Application |
|---|---|---|---|
| mGapdh | F | ACCACAGTCCATGCCATCAC | Semi-quantitative analysis in mouse |
| | R | TCCACCACCCTGTTGCTGTA | |
| hHPRT | F | ACCCCACGAAGTGTTGGATA | Semi-quantitative analysis in human cells |
| | R | AAGCAGATGGCCACAGAACT | |
| mDnm2 | F | GGTGGTCAAGCTGAAAGAG | Semi-quantitative analysis in MEF and EcoNI digestion profile |
| | R | GCTGTCAGCACGAACCAGTA | |
| mDnm1 | F | AGATGGAGCGAATTGTGACC | Semi-quantitative analysis in mouse |
| | R | GAATGACCTGGTTCCCTGAA | |
| mDnm3 | F | ATGCTCCGAATGTACCAAGC | Semi-quantitative analysis in mouse |
| | R | GAGGGGAGCACTTATCGTCA | |
| mDnm2speMut | F | AATTGTCACCACCTACATCA | Specific amplification of the mutated Dnm2 in mouse |
| | R | GGTTTGTGTTGATGTACGACTGC | |
| mDnm2speWT | F | AATTGTCACCACCTACATCT | Specific amplification of the WT Dnm2 in mouse |
| | R | GGTTTGTGTTGATGTACGACTGC | |
| mDnm2g | F | CTGCGAGAGGAGACCGAGC | Genotyping (knock-in mice) |
| | R | GCTGAGCACTGGAGAGTGTATGG | |
| hDnm2 | F | GAAAAAGCAGGTCGTCAAGC | Semi-quantitative analysis in human cells and PfoI digestion profile |
| | R | ATTGGGGATGGCTCTCTT | |

Legend:
F: Forward.
R: Reverse.
Dnm2: Dynamin 2.
Gapdh: Glyceraldehyde 3-phosphate dehydrogenase.

The half of the PCR products was used for restriction enzyme digestion with 2U of EcoNI (New England Biolabs, France) or PfoI (ThermoFisher Scientific, France) for 2 h at 37° C. Image acquisition of PCR products after agarose gel electrophoresis was performed using G-box (Ozyme, France) and associated-signal was quantified using ImageJ Software (NIH; http://rsbweb.nih.gov/ij). DNA sequencing was performed on 20 ng DNA/100 bp with 5 pmol of primers (Eurofins, France).

Protein Extraction and Western Blot

Cell pellets and frozen Tibialis anterior muscles (TA) were homogenized in lysis buffer containing 50 mM of Tris-HCl pH 7.5, 150 mM NaCl, 1 mM EDTA, NP40 1%) supplemented with protease inhibitor cocktail 1% (Sigma-Aldrich, France). In addition, Tibialis anterior muscles were mechanically homogenized in the lysis buffer using Fastprep Lysing Matrix D and Fastprep apparatus (MP Biomedical, France). After centrifugation (14,000 g, 4° C., 15 min), protein concentration in the supernatant was determined with the BCA Protein Assay Kit (Thermo Scientific Pierce, France). Twenty μg of protein were mixed with loading buffer (50 mM Tris-HCl, SDS 2%, glycerol 10%, β-mercaptoethanol 1% and bromophenol blue) and denaturated at 90° C. for 5 min. Protein samples were separated on SDS-PAGE 10% and transferred onto PVDF membranes (0.45 μm pore size, Life Technologies) overnight at 100 mA at 4° C. Membranes were blocked for 1 h at room temperature in PBS containing non-fat dry milk 5% and Tween20 0.1% and then exposed to the following primary antibodies: rabbit polyclonal anti-Dynamin 2 (Abcam ab3457, United Kingdom) and rabbit polyclonal anti-GAPDH (Santa Cruz, France) in PBS-Tween20 0.1%, milk 1% overnight at 4° C. Membranes were rinsed in PBS-Tween20 0.1% and incubated 1 h with secondary horseradish peroxidase-conjugated antibodies (anti-rabbit from Jackson ImmunoResearch, United Kingdom) in PBS-Tween20 0.1%. Chemiluminescence was detected using ECL detection Kit (Merck-Millipore, Germany) in G-Box (Ozyme, France) and associated-signal quantification was performed using ImageJ software.

AAV Production and In Vivo AAV Injection

AAV2/1 pseudotyped vectors were prepared by transfection in 293 cells using the pSMD2-Dnm2-PTM plasmid, the pXX6 plasmid coding for the adenoviral sequences essential for AAV production, and the pRepCAp plasmid coding for AAV1 capsid. Vector particles were purified on iodixanol gradient and concentrated on Amicon Ultra-15 100K columns (Merck-Millipore). The particle titer (number of viral genomes (vg)/ml) was determined by quantitative PCR. Wild-type and heterozygous KI-Dnm2$^{R465W}$ mice at 1 month of age were injected under isoflurane anesthesia. Two intramuscular injections (30 μl/TA, within 24 h interval) of AAV-sh9, AAV-sh10, or AAV-nosh (negative control without shRNA sequence in the viral genome) were performed in 2 TA using 29G needle at $10^{11}$ vg/muscle. Animal studies conform to the French laws and regulations concerning the use of animals for research and were approved by an external Ethical committee (approval n°00351.02 delivered by the French Ministry of Higher Education and Scientific Research).

Muscle Contractile Properties

The isometric contractile properties of TA muscles were studied in situ on mice anesthetized with 60 mg/kg pentobarbital. The distal tendon of the TA muscle was attached to a lever arm of a servomotor system (305B Dual-Mode Lever, Aurora Scientific). The sciatic nerve was stimulated by a bipolar silver electrode using a supramaximal (10 V) square wave pulse of 0.1 ms duration. Absolute maximal isometric tetanic force (P0) was measured during isometric contractions in response to electrical stimulation (frequency of 25-150 Hz; train of stimulation of 500 ms). All isometric contraction measurements were made at optimal muscle length (L0) at which P0 was obtained. TA muscles were weighted and specific force (sP0) was calculated by dividing P0 by muscle weight.

Histomorphological Analyses

Mice were sacrificed by cervical dislocation under isoflurane anesthesia. TA muscles were frozen in liquid nitrogen-cooled isopentane. Transverse sections of TA muscle (8 µm thick) were stained with hematoxylin and eosin (HE) and reduced nicotinamide adenine dinucleotide-tetrazolium reductase (NADH-TR) by standard methods. Light microscopy were performed using an upright microscope (DMR, Leica) and images were captured using a monochrome camera (DS-Ri1, Nikon) and NIS-Elements BR software (Nikon, France). For all imaging, exposure settings were identical between compared samples and viewed at room temperature. Fiber size distribution was determined on TA muscle sections immunocytochemically labelled with laminin by measuring Ferret diameter using ImageJ software.

Immunocytochemistry

Cells and TA cryosections (8 µm thick) were fixed in paraformaldehyde 4% (15 min at room temperature). After washing in PBS, cells and cryosections were permeabilized in Triton X-100 0.5% in PBS for 10 min at room temperature and blocked in PBS-Triton X-100 0.1%, BSA 5% and Donkey serum 5% for 30 min. Samples were incubated with primary antibodies: rabbit anti-C-terminal Dynamin 2 (Abcam ab3457) or rabbit-anti Laminin (Abcam ab11575) overnight at 4° C., in PBS with Triton X-100 0.1% and BSA 1%. After PBS-Triton X100 0.1% washes, samples were incubated with Donkey anti-rabbit Alexa 488 secondary antibody (Life Technologies, France) for 60 min at room temperature. The slides were mounted with VECTASHIELD mounting medium (Vector Laboratories, United Kingdom). Images were acquired using either axiophot microscope (Zeiss) or confocal microscope (Olympus FV-1000).

Transferrin Uptake Assay

Two healthy control cell lines (C1 and C2) and one patient-derived cell line expressing the p.R465W mutation were used 48 h after transfection with siRNA. Cells were cultured in DMEM without FCS at 37° C. for 45 min. Transferrin-AlexaFluor488 (Life Technologies, France) was added at 40 µg/ml and cells were incubated at 37° C. for 15 min. Cells were washed 3 times with PBS and fixed in paraformaldehyde 4% at room temperature for 15 min. Stacks of cell images (0.5 µm interval) were gained using a confocal Leica SP2 microscope. Fluorescent-positive surface was quantified on stack projection using ImageJ software and normalized to the total cell surface.

Results

Identification of Allele-Specific siRNA in Heterozygous Cells

The p.R465W DNM2 mutation was used to construct the KI-Dnm2$^{R465W}$ mouse model. In mouse, this missense mutation corresponds to a single point mutation A>T in exon 11. A screening for allele specific siRNA silencing the mutated Dnm2 allele without affecting the WT one was performed in Mouse Embryonic Fibroblasts (MEF) cultured from heterozygous (HTZ) KI-Dnm2 mice. Using a RT-PCR assay developed to discriminate the WT and mutated allele after restriction enzyme digestion of amplicon, we assessed allele-specific properties of 12 siRNA among the 19 possible siRNA (FIG. 1A). In FIG. 1A. siRNA sense strands are represented. It is the other siRNA strand (the antisense strand) that binds by complementarity to the target mutant mRNA). At low concentration (20 nM), scramble siRNA-transfected cells and non-transfected cells show a Mutant/WT ratio equal to 1 in agreement with similar expression of both WT and mutated alleles (FIG. 1B). Among the 12 assessed siRNA, 6 siRNA (si9, si10, si11, si12, si15, si16) exhibit allele-specific silencing properties as demonstrated by significantly reduced Mutant/WT ratio compared to scramble siRNA-transfected control cells (FIG. 1B). Within those 6 siRNA, the position of the mismatch is respectively located at position N9, N10, N11, N12, N15 or N16 from 5' end of the sense strand of AS-siRNA.

In order to establish allele-specific silencing, further analyses were pursued for 2 of the most efficient siRNA, i.e. si9 and si10 at high concentration (100 nM). After 48 h, total Dnm2-mRNA expression (WT+mutated) is reduced around 50% for both siRNA (FIG. 2A). Sequencing of the amplicons showed HTZ Dnm2 sequence in scramble-transfected cells and only WT sequence in si9- and si10-transfected cells (FIG. 2B). Allele-specificity of the two siRNA against the mutated allele is demonstrated by the measured mutant/WT ratio around 0.2 (FIG. 2C) and is confirmed by quantification of the expression level of both Mutant and WT mRNA relative to the housekeeping Gapdh mRNA expression (Data not shown). At protein level, both si9 and si10 induced a decrease in Dnm2 expression level around 50% as established by western blot (FIG. 2D) without modifying Dnm2 subcellular localization (Data not shown). Under these conditions, si9 and si10 do not affect expression of Dnm1 and Dnm3 transcripts (Data not shown). Altogether, these data validate si9 and si10 as efficient allele-specific siRNA since both specifically knock-down the mutated Dnm2 transcript without affecting the WT resulting to a remaining expression of the half of the Dnm2 transcript and protein. The ability of 100 nM of si9 and si10 to specifically silence the mutant allele was confirmed by RT-PCR in immortalized mouse myoblasts derived from HTZ KI-Dnm2 mice (FIG. 3).

Restoration of the Muscle Phenotype in KI-Dnm2 Mice

Muscle phenotype in TA muscle from HTZ KI-Dnm2 mice is fully established at 2 months of age and includes impairment of contractile properties, muscle atrophy due to decrease in fibre size, and morphological abnormalities on oxidative staining. Adeno-associated virus (AAV) vectors expressing shRNA corresponding to si9 and si10 and a control AAV without shRNA sequence (AAV-nosh) were constructed for in vivo evaluation. AAV were injected intramuscularly in TA muscles of HTZ KI-Dnm2 mice at 1 month of age and muscle phenotype was investigated 3 months later. Compared to WT TA, a significant decrease around 30% in mass, 40% in absolute force and 15% in specific force is present in nosh-injected HTZ muscles (FIG. 4). Expression of sh9 fully restored absolute and specific force to the WT values. Muscle mass is also largely increased compared to noSh muscles (+30%) but remains slightly lower than WT muscle mass (−10%) in sh9-injected mice. Significant restoration is also achieved by expression of sh10 by increasing absolute and specific forces and muscle mass. (FIG. 4).

Expression level of Dnm2 transcript was quantified by RT-PCR showing a significant decrease (−30%) in the Dnm2 content in sh9-expressing muscle compared to nosh values whereas statistical significance is not reached in muscle expressing sh10 (FIG. 5A). In agreement, sequencing of Dnm2 amplicons showed a HTZ sequence at the mutated nucleotide position in AAV-transduced muscles with a substantial reduction of the peak corresponding to the mutated nucleotide with sh9 and to a lesser extent with sh10 (FIG. 5B). Allele-specific silencing was evaluated by quantifying Mutant/WT ratio using RT-PCR and EcoNI digestion profile. An expected reduction of Mutant/WT ratio was achieved with values reaching around 0.5 and 0.7 for sh9 and sh10, respectively (FIG. 5C). Specific silencing of the mutated transcript achieved by sh9 was also shown by quantification of digested products corresponding to WT and Mutant mRNA relative to Gapdh expression and was confirmed by a second RT-PCR assay using primers designed for specific amplification of either WT or mutated allele (data not shown).

The restoration of phenotype at histological level was further evaluated. When compared to WT muscle, HTZ TA muscles show a reduction of fibre size illustrated on HE staining and central accumulation of oxidative material on DPNH oxidative staining (FIG. 5D). Fibre size appeared higher in sh9-expressing muscles and abnormalities were not visible on DPNH staining. In contrast morphological abnormalities were still present in sh10-expressing TA. Calculation of frequency of fibre size (FIG. 5E) confirm the total rescue of these parameters only in HTZ TA muscles transduced by sh9-AAV. Altogether, these data demonstrate the capability of sh9 to fully reverse muscle phenotype in mice after a 3-month treatment whereas sh10 only induced a partial restoration under the same conditions. However, optimisation of the amount of vector, time of treatment or other adaptations well within the general knowledge of the skilled person may be implemented for improving this restoration.

Allele-Specific Silencing in Patient-Derived Cells

The Dnm2 target sequence for si9 and si10 shows 79% identity (15 out of 19 bp) between mouse and human sequence. Human-specific si9 and si10 were produced for in vitro evaluation in one patient-derived fibroblast cell line expressing the p.R465W mutation. Dnm2 mRNA content is reduced around 50% in cells transfected with si9 for 48 h at 50 nM (FIG. 6A). Amplicon sequencing confirms disappearance of the mutated mRNA in si9-transfected fibroblasts compared to scramble- and si10-transfected cells still expressing a mix of WT and mutated DNM2 (FIG. 6B). We used a semi-quantitative RT-PCR assay developed to discriminate the WT and mutated allele after PfoI digestion of amplicon. Using this assay, mutant/WT ratio is equal to 1 for non-transfected and scramble-transfected cells and significantly reduced to 0.8 by si10 and 0.2 by si9 (FIG. 6C). Transfection of both si9 and si10 for 48 h resulted in reduction of DNM2 protein content as demonstrated by western-blot (FIG. 6D). Given that si9 exhibited all the expected properties of allele-specific siRNA in human cells, si9 was consequently further investigated at higher dose (100 nM). At this dose, expression of DNM2 transcript was still reduced around 50% (FIG. 7A) and allele-specificity against the mutated DNM2 mRNA is maintained (FIG. 7B) without evident cell toxicity (FIG. 7C). Basic Local Alignment Search Tool (BLAST) used to identify potential off target for si9 (sense and antisense strands) showed SLC9A8 as the nearest sequence with 68% identity corresponding to complete identity on 13 consecutive nucleotides. We checked for potential si9-induced silencing of SLC9A8 mRNA by RT-PCR 48 hours after transfection of siRNA at 100 mM. Compared to Scramble siRNA, si9 does not affect expression of the SLC9A8 transcript (data not shown).

si9 properties was finally evaluated by investigating functional rescue in patient-derived cells. Clathrin-mediated endocytosis is impaired in fibroblast from patient. A fluorescent-transferrin uptake assay was used to evaluate capability of si9 to restore normal endocytosis. Compared to 2 healthy control cell lines, 15 minutes transferrin uptake is reduced in scramble-transfected cells from the CNM patient but achieved normal value in cells transfected with si9 for 48 hours before assay (FIG. 8A). Transfection of si9 in control cell lines does not impact clathrin-mediated endocytosis (FIG. 8B) in agreement with absence of effect on WT Dnm2 mRNA.

Discussion

Allele-specific silencing by RNAi benefits from outstanding specificity of RNA interference process mediated by siRNA able to discriminate two sequences, even when differing by a single nucleotide. This property qualified allele-specific RNAi to target dominant mutations resulting to single nucleotide substitution representing the majority of the 24 DNM2 mutations identified in patients suffering from AD-CNM, especially for the most frequent of them (30% of patients), i.e. the p.R465W mutation. The above results demonstrated the efficiency of allele-specific RNAi against the p.R465W mutation as therapeutic strategy for DNM2-related CNM through rescue animal model and in patient-derived cells.

In a context of dominant inherited disease in which WT and mutated alleles are similarly expressed, allele-specific siRNA are expected to reduced expression of target mRNA and protein around 50% resulting from silencing of the mutated allele without affecting the WT. This is the case in this study for si9 in murine and human cells.

As-siRNA Targeting the Allele of the DNM2 Gene Comprising a Non-Pathological Polymorphism Materials and Methods Cell Cultures Human skin fibroblasts from one DNM2-linked CNM patient harbouring the p.R465W mutation were cultured at 37° C. (5% CO2) in Dulbecco's modified Eagle's medium (DMEM) containing 10% foetal calf serum (FCS) supplemented with penicillin, streptomycin, L-glutamate, and sodium pyruvate. Experiments were performed on immortalized cell population after transduction with lentivirus expressing human telomerase reverse transcriptase (hTERT). For transfection, cells were grown to 70% confluency and transfected with siRNA using JetPrime transfection reagent according to the manufacturer's protocol (Polyplus Transfection, France). Concentration of siRNA for each experiment are indicated in figure legend. Scramble siRNA (Eurogentec, Belgium) was used as control. Cells were harvested 48 h later for RNA and extraction and RT-PCR analysis.

Total RNA Extraction and cDNA Analysis

Total RNA was isolated using RNA easy kits (Qiagen, France) according to the manufacturer's protocol. Cells were passed through a 22G syringe several times for disruption in the lysis buffer. Total RNA (1 µg) was submitted to reverse transcription using the Superscript III reverse transcriptase kit (Life Technologies) using hexamer primers. cDNA were amplified by PCR under the following conditions: 96° C. for 5 min, cycles of 30 s at 96° C., 30 s at the appropriate temperature (58 to 62° C.), 30 s to 1 min at 72° C., and a final step of 7 min at 72° C. Twenty seven cycles were performed to amplify HPRT, 27 for semi-quantitative analysis of DNM2, 30 for restriction enzyme digestion of the DNM2 amplicon. Sequences of all the primers used are indicated in the following table:

Table: Primers used in this study

| Target | | Sequence (5'-3') | Application |
|---|---|---|---|
| hHPRT | F | ACCCCACGAAGTGTTGGATA | Semi-quantitative analysis in human cells |
| | R | AAGCAGATGGCCACAGAACT | |
| hDNM2 | F | GAAAAAGCAGGTCGTCAAGC | Semi-quantitative analysis in human cells and |
| | R | ATTGGGGATGGCTCTCTT | PfoI Semi digestion profile |

Legend:
F: Forward.
R: Reverse.
DNM2: Dynamin 2.
HPRT: hypoxanthine guanine phosphoribosyl transferase The half of the PCR products was used for restriction enzyme digestion with 2U of BglI (New England Biolabs, France) for 2 h at 37° C. Image acquisition of PCR products after agarose gel electrophoresis was performed using G-box (Ozyme, France) and associated-signal was quantified using ImageJ Software (NIH; http://rsbweb.nih.gov/ij).

Results

Identification of Allele-Specific siRNA by Targeting a Heterozygous Non-Pathogenic Polymorphism The patient-derived cells harbour the p.R465W DNM2 mutation and are heterozygous for the single nucleotide polymorphism (SNP) rs2229920 (C and T) corresponding to one basis of the codon encoding the amino-acid at position 713 in the DNM2 protein sequence. By sequencing the DNM2 mRNA, we showed that the mutation is in frame with the C version of the polymorphism. The presence of the HTZ SNP allowed to screen for efficient AS-siRNA against the two possible versions of the SNP (C and T). Two siRNA against the C (including the mismatch at position 16 or 17, i.e. si16-713C and si17-713C, respectively) and one siRNA against the T (including the mismatch at position 17 called si17-713T) were assessed. Cells were transfected with 30 nM of siRNA for 48 hours before RT-PCR analysis. The 3 tested siRNA are efficient to decrease the expression of the DNM2 transcript when compared to cells transfected with Scramble siRNA or non-transfected cells (FIG. 9A). Quantification of the DNM2 transcript relative to HPRT mRNA used as housekeeping gene (FIG. 9B) indicates that a mismatch at position 17 are more efficient compared to position 16. Using a RT-PCR assay developed to discriminate the allele C and the allele T after restriction enzyme digestion of amplicon, we assessed allele-specific properties of these 3 siRNA at 30 nM for 48 hours.

Scramble siRNA-transfected cells and non-transfected cells show a C (Mutant)/T (WT) ratio equal to 1 in agreement with similar expression of both WT and mutated alleles (FIG. 10). The ratio decreases when siRNA against the C are used but increase when siRNA against the T is used (FIG. 10B left panel). Allele-specificity of these 3 siRNA was confirmed by quantifying the mRNA level harbouring the T nucleotide relative to HPRT expression showing a decrease only when the si17-713T is used (FIG. 10B, right panel).

Modification of the Sequence of the Allele-Specific siRNA Against the C Allele of the Non-Pathogenic Polymorphism With the objective to increase siRNA efficiency, length of the si17-713C was modified by adding nucleotides in 5' or 3' (FIG. 11A). When transfected at 50 nM for 48 hours, all the 3 modified siRNA are able to decrease expression of the DNM2 transcript compared to scramble siRNA (FIG. 11C) but, among them, the si713C-17/21 appears less efficient (although still of interest with around 30% of decrease). Allele-specificity was assessed using RT-PCR followed by BglI digestion. In non-transfected cells and in cells transfected with scramble siRNA, the calculated allele C/allele T ratio is around 1 in agreement with similar expression level of both alleles. As expected, transfection of 50 nM of all the modified AS-siRNA against the C for 48 hours leads to the decrease in the allele C/allele T ratio.

Discussion

In case of dominant diseases in which several causing mutations have been identified, two Allele-specific silencing by RNAi strategies may be developed. The first strategy corresponds to personalized therapy by developing AS-siRNA against each identified mutation as developed for the p.R465W DNM2 mutation causing AD-CNM. The second strategy is to develop AS-siRNA against a non-pathogenic variant associated with the disease. Here, we show that this pan-mutation strategy may be developed for the DNM2-linked CNM by targeting a common non-pathogenic single nucleotide polymorphism (SNP) present in the coding region of the DNM2 transcript. Given that this SNP is frequently found in heterozygous state (C on one allele and T on the other one), AS-siRNA against the SNP enable silencing of all the mutated transcript by using the AS-siRNA against the version of the SNP in frame with the mutation.

Here, we have identified several efficient AS-siRNA against the two possible version of the SNP rs2229920 (either the C allele or the T allele). This results highlight for the first time the possibility to target all the dominant DNM2 mutations whatever the resulting disease (CNM, CMT or HSP) and also to decrease, in a controlled manner, the DNM2 expression in diseases associated with an overexpression of this protein (X-linked myotubular myopathy, pancreas and prostate cancers).

The invention claimed is:

1. An allele specific siRNA (AS-siRNA) that comprises a sequence mismatch and is able to silence the expression of only one allele of a heterozygous DNM2 gene in a cell, wherein the DNM2 gene is heterozygous for the presence of a non-pathological polymorphism, wherein the non-pathological polymorphism is rs2229920 (C or T) or rs12461992 (A or T), and wherein the AS-siRNA targets a region of the allele comprising said non-pathological polymorphism.

2. The AS-siRNA of claim 1, wherein the AS-siRNA is of 19-23 base pairs in length.

3. The AS-siRNA of claim 1 wherein the DNM2 gene is heterozygous for the presence of a disease-causing mutation.

4. The AS-siRNA of claim 3, wherein said non-pathological polymorphism is on the same allele as the disease-causing mutation.

5. The AS-siRNA of claim 3, wherein the disease-causing mutation is 1393C>T; c.1105C>T, c.1106G>A, c.1856C>T or c.1948G>A.

6. The AS-siRNA of claim 1, wherein the AS-siRNA is of 19 base pairs in length and wherein the position of the sequence mismatch is located at position N16 or N17 from the 5' end of the sense strand of said AS-siRNA.

7. The AS-siRNA of claim 1, wherein the AS-siRNA comprises a sense strand selected from the group consisting of : SEQ ID NO:1, SEQ ID NO:2, SEQ ID NO:3 and SEQ ID NO:4.

8. The AS-siRNA of claim 1, wherein the AS-siRNA reduces expression of DNM2 mRNA and/or DNM2 protein by 20-60%.

9. A vector encoding the AS-siRNA according to claim 1.

10. An isolated target cell, which is transfected or transduced with the vector according to claim 9.

11. An in vitro method for silencing the expression of a mutated allele of a DNM2 gene without silencing the expression of the wild type allele of the DNM2 gene in a target cell, comprising introducing in said target cell an AS-siRNA according to claim 1 or a vector encoding the AS-siRNA.

12. A method for ameliorating a disease selected from autosomal dominant centronuclear myopathy, myotubular myopathy, and Duchenne muscular dystrophy, in a subject in need thereof, comprising
administering to the subject a therapeutic amount of the AS-siRNA of claim 1, or a vector encoding the AS-siRNA, or a cell transfected or transduced with the vector.

13. An AS-siRNA that comprises a sense strand selected from the group consisting of : SEQ ID NO:5, SEQ ID NO:6, SEQ ID NO:7, SEQ ID NO:8, SEQ ID NO:9 and SEQ ID NO:10.

* * * * *

SEQUENCE LISTING

<160> NUMBER OF SEQ ID NOS: 59

<210> SEQ ID NO 1
<211> LENGTH: 19
<212> TYPE: RNA
<213> ORGANISM: artificial

```
<220> FEATURE:
<223> OTHER INFORMATION: Synthetic Hs-si17C

<400> SEQUENCE: 1
ucauggagga gucggccga                                                19

<210> SEQ ID NO 2
<211> LENGTH: 19
<212> TYPE: RNA
<213> ORGANISM: artificial
<220> FEATURE:
<223> OTHER INFORMATION: Synthetic Hs-si17T

<400> SEQUENCE: 2
ucauggagga gucggcuga                                                19

<210> SEQ ID NO 3
<211> LENGTH: 19
<212> TYPE: RNA
<213> ORGANISM: artificial
<220> FEATURE:
<223> OTHER INFORMATION: Synthetic Hs-si16C

<400> SEQUENCE: 3
cauggaggag ucggccgac                                                19

<210> SEQ ID NO 4
<211> LENGTH: 19
<212> TYPE: RNA
<213> ORGANISM: artificial
<220> FEATURE:
<223> OTHER INFORMATION: Synthetic Hs-si16T

<400> SEQUENCE: 4
cauggaggag ucggcugac                                                19

<210> SEQ ID NO 5
<211> LENGTH: 19
<212> TYPE: RNA
<213> ORGANISM: artificial
<220> FEATURE:
<223> OTHER INFORMATION: Synthetic Hs-si9-R465

<400> SEQUENCE: 5
cuuacaucug ggaacggga                                                19

<210> SEQ ID NO 6
<211> LENGTH: 19
<212> TYPE: RNA
<213> ORGANISM: artificial
<220> FEATURE:
<223> OTHER INFORMATION: Synthetic Hs-si10-R465

<400> SEQUENCE: 6
acuuacaucu gggaacggg                                                19

<210> SEQ ID NO 7
<211> LENGTH: 19
<212> TYPE: RNA
<213> ORGANISM: artificial
<220> FEATURE:
<223> OTHER INFORMATION: Synthetic Hs-si11-R465

<400> SEQUENCE: 7
cacuuacauc ugggaacgg                                                19
```

```
<210> SEQ ID NO 8
<211> LENGTH: 19
<212> TYPE: RNA
<213> ORGANISM: artificial
<220> FEATURE:
<223> OTHER INFORMATION: Synthetic Hs-si12-R465

<400> SEQUENCE: 8
ccacuuacau cugggaacg                                              19

<210> SEQ ID NO 9
<211> LENGTH: 19
<212> TYPE: RNA
<213> ORGANISM: artificial
<220> FEATURE:
<223> OTHER INFORMATION: Synthetic Hs-si15-R465

<400> SEQUENCE: 9
ucaccacuua caucuggga                                              19

<210> SEQ ID NO 10
<211> LENGTH: 19
<212> TYPE: RNA
<213> ORGANISM: artificial
<220> FEATURE:
<223> OTHER INFORMATION: Synthetic Hs-si16-R465

<400> SEQUENCE: 10
gucaccacuu acaucuggg                                              19

<210> SEQ ID NO 11
<211> LENGTH: 38
<212> TYPE: RNA
<213> ORGANISM: artificial
<220> FEATURE:
<223> OTHER INFORMATION: Synthetic WT murine DNM2 mRNA

<400> SEQUENCE: 11
auugucacca ccuacaucag ggagcgagaa gggagaac                         38

<210> SEQ ID NO 12
<211> LENGTH: 38
<212> TYPE: RNA
<213> ORGANISM: artificial
<220> FEATURE:
<223> OTHER INFORMATION: Synthetic R465W murine DNM2 mRNA

<400> SEQUENCE: 12
auugucacca ccuacaucug ggagcgagaa gggagaac                         38

<210> SEQ ID NO 13
<211> LENGTH: 19
<212> TYPE: RNA
<213> ORGANISM: artificial
<220> FEATURE:
<223> OTHER INFORMATION: Synthetic Mm-si1-R465W

<400> SEQUENCE: 13
ugggagcgag aagggagaa                                              19

<210> SEQ ID NO 14
<211> LENGTH: 19
<212> TYPE: RNA
<213> ORGANISM: artificial
<220> FEATURE:
<223> OTHER INFORMATION: Synthetic Mm-si2-R465W
```

```
<400> SEQUENCE: 14
cugggagcga aagggaga                                                    19

<210> SEQ ID NO 15
<211> LENGTH: 19
<212> TYPE: RNA
<213> ORGANISM: artificial
<220> FEATURE:
<223> OTHER INFORMATION: Synthetic Mm-si3-R465W

<400> SEQUENCE: 15
ucugggagcg agaagggag                                                   19

<210> SEQ ID NO 16
<211> LENGTH: 19
<212> TYPE: RNA
<213> ORGANISM: artificial
<220> FEATURE:
<223> OTHER INFORMATION: Synthetic Mm-si4-R465W

<400> SEQUENCE: 16
aucugggagc gagaaggga                                                   19

<210> SEQ ID NO 17
<211> LENGTH: 19
<212> TYPE: RNA
<213> ORGANISM: artificial
<220> FEATURE:
<223> OTHER INFORMATION: Synthetic Mm-si5-R465W

<400> SEQUENCE: 17
caucugggag cgagaaggg                                                   19

<210> SEQ ID NO 18
<211> LENGTH: 19
<212> TYPE: RNA
<213> ORGANISM: artificial
<220> FEATURE:
<223> OTHER INFORMATION: Synthetic Mm-si6-R465W

<400> SEQUENCE: 18
acaucuggga gcgagaagg                                                   19

<210> SEQ ID NO 19
<211> LENGTH: 19
<212> TYPE: RNA
<213> ORGANISM: artificial
<220> FEATURE:
<223> OTHER INFORMATION: Synthetic Mm-si7-R465W

<400> SEQUENCE: 19
uacaucuggg agcgagaag                                                   19

<210> SEQ ID NO 20
<211> LENGTH: 19
<212> TYPE: RNA
<213> ORGANISM: artificial
<220> FEATURE:
<223> OTHER INFORMATION: Synthetic Mm-si8-R465W

<400> SEQUENCE: 20
cuacaucugg gagcgagaa                                                   19
```

-continued

```
<210> SEQ ID NO 21
<211> LENGTH: 19
<212> TYPE: RNA
<213> ORGANISM: artificial
<220> FEATURE:
<223> OTHER INFORMATION: Synthetic Mm-si9-R465W

<400> SEQUENCE: 21
ccuacaucug ggagcgaga                                                  19

<210> SEQ ID NO 22
<211> LENGTH: 19
<212> TYPE: RNA
<213> ORGANISM: artificial
<220> FEATURE:
<223> OTHER INFORMATION: Synthetic Mm-si10-R465W

<400> SEQUENCE: 22
accuacaucu gggagcgag                                                  19

<210> SEQ ID NO 23
<211> LENGTH: 19
<212> TYPE: RNA
<213> ORGANISM: artificial
<220> FEATURE:
<223> OTHER INFORMATION: Synthetic Mm-si11-R465W

<400> SEQUENCE: 23
caccuacauc ugggagcga                                                  19

<210> SEQ ID NO 24
<211> LENGTH: 19
<212> TYPE: RNA
<213> ORGANISM: artificial
<220> FEATURE:
<223> OTHER INFORMATION: Synthetic Mm-si12-R465W

<400> SEQUENCE: 24
ccaccuacau cugggagcg                                                  19

<210> SEQ ID NO 25
<211> LENGTH: 19
<212> TYPE: RNA
<213> ORGANISM: artificial
<220> FEATURE:
<223> OTHER INFORMATION: Synthetic Mm-si13-R465W

<400> SEQUENCE: 25
accaccuaca ucugggagc                                                  19

<210> SEQ ID NO 26
<211> LENGTH: 19
<212> TYPE: RNA
<213> ORGANISM: artificial
<220> FEATURE:
<223> OTHER INFORMATION: Synthetic Mm-si14-R465W

<400> SEQUENCE: 26
caccaccuac aucugggag                                                  19

<210> SEQ ID NO 27
<211> LENGTH: 19
<212> TYPE: RNA
<213> ORGANISM: artificial
<220> FEATURE:
<223> OTHER INFORMATION: Synthetic Mm-si15-R465W
```

```
<400> SEQUENCE: 27
ucaccaccua caucuggga                                            19

<210> SEQ ID NO 28
<211> LENGTH: 19
<212> TYPE: RNA
<213> ORGANISM: artificial
<220> FEATURE:
<223> OTHER INFORMATION: Synthetic Mm-si16-R465W

<400> SEQUENCE: 28
gucaccaccu acaucuggg                                            19

<210> SEQ ID NO 29
<211> LENGTH: 19
<212> TYPE: RNA
<213> ORGANISM: artificial
<220> FEATURE:
<223> OTHER INFORMATION: Synthetic Mm-si17-R465W

<400> SEQUENCE: 29
ugucaccacc uacaucugg                                            19

<210> SEQ ID NO 30
<211> LENGTH: 19
<212> TYPE: RNA
<213> ORGANISM: artificial
<220> FEATURE:
<223> OTHER INFORMATION: Synthetic Mm-si18-R465W

<400> SEQUENCE: 30
uugucaccac cuacaucug                                            19

<210> SEQ ID NO 31
<211> LENGTH: 19
<212> TYPE: RNA
<213> ORGANISM: artificial
<220> FEATURE:
<223> OTHER INFORMATION: Synthetic Mm-si19-R465W

<400> SEQUENCE: 31
auugucacca ccuacaucu                                            19

<210> SEQ ID NO 32
<211> LENGTH: 12
<212> TYPE: DNA
<213> ORGANISM: artificial
<220> FEATURE:
<223> OTHER INFORMATION: Synthetic Dnm2 amplicons SEQ
<220> FEATURE:
<221> NAME/KEY: misc_feature
<222> LOCATION: (6)..(6)
<223> OTHER INFORMATION: n=a or t

<400> SEQUENCE: 32
acatcnggga gc                                                   12

<210> SEQ ID NO 33
<211> LENGTH: 12
<212> TYPE: DNA
<213> ORGANISM: artificial
<220> FEATURE:
<223> OTHER INFORMATION: Synthetic Dnm2 amplicons SEQ

<400> SEQUENCE: 33
acatcaggga gc                                                   12
```

```
<210> SEQ ID NO 34
<211> LENGTH: 21
<212> TYPE: DNA
<213> ORGANISM: artificial
<220> FEATURE:
<223> OTHER INFORMATION: Synthetic si-17C/21

<400> SEQUENCE: 34
tcatggagga gtcggccgac c                                          21

<210> SEQ ID NO 35
<211> LENGTH: 21
<212> TYPE: RNA
<213> ORGANISM: artificial
<220> FEATURE:
<223> OTHER INFORMATION: Synthetic Si-17C/21 ARN

<400> SEQUENCE: 35
ucauggagga gucggccgac c                                          21

<210> SEQ ID NO 36
<211> LENGTH: 21
<212> TYPE: DNA
<213> ORGANISM: artificial
<220> FEATURE:
<223> OTHER INFORMATION: Synthetic Si-19C/21

<400> SEQUENCE: 36
cctcatggag gagtcggccg a                                          21

<210> SEQ ID NO 37
<211> LENGTH: 21
<212> TYPE: RNA
<213> ORGANISM: artificial
<220> FEATURE:
<223> OTHER INFORMATION: Synthetic Si-19C/21 ARN

<400> SEQUENCE: 37
ccucauggag gagucggccg a                                          21

<210> SEQ ID NO 38
<211> LENGTH: 22
<212> TYPE: DNA
<213> ORGANISM: artificial
<220> FEATURE:
<223> OTHER INFORMATION: Synthetic Si-20C/22

<400> SEQUENCE: 38
gcctcatgga ggagtcggcc ga                                         22

<210> SEQ ID NO 39
<211> LENGTH: 22
<212> TYPE: RNA
<213> ORGANISM: artificial
<220> FEATURE:
<223> OTHER INFORMATION: Synthetic Si-20C/22 ARN

<400> SEQUENCE: 39
gccucaugga ggagucggcc ga                                         22

<210> SEQ ID NO 40
<211> LENGTH: 20
<212> TYPE: DNA
<213> ORGANISM: artificial
<220> FEATURE:
<223> OTHER INFORMATION: Synthetic Primer mGapdh (F)
```

<400> SEQUENCE: 40
accacagtcc atgccatcac        20

<210> SEQ ID NO 41
<211> LENGTH: 20
<212> TYPE: DNA
<213> ORGANISM: artificial
<220> FEATURE:
<223> OTHER INFORMATION: Synthetic Primer mGapdh (R)

<400> SEQUENCE: 41
tccaccaccc tgttgctgta        20

<210> SEQ ID NO 42
<211> LENGTH: 20
<212> TYPE: DNA
<213> ORGANISM: artificial
<220> FEATURE:
<223> OTHER INFORMATION: Synthetic Primer hHPRT (F)

<400> SEQUENCE: 42
accccacgaa gtgttggata        20

<210> SEQ ID NO 43
<211> LENGTH: 20
<212> TYPE: DNA
<213> ORGANISM: artificial
<220> FEATURE:
<223> OTHER INFORMATION: Synthetic Primer hHPRT (R)

<400> SEQUENCE: 43
aagcagatgg ccacagaact        20

<210> SEQ ID NO 44
<211> LENGTH: 19
<212> TYPE: DNA
<213> ORGANISM: artificial
<220> FEATURE:
<223> OTHER INFORMATION: Synthetic Primer mDnm2 (F)

<400> SEQUENCE: 44
ggtggtcaag ctgaaagag        19

<210> SEQ ID NO 45
<211> LENGTH: 20
<212> TYPE: DNA
<213> ORGANISM: artificial
<220> FEATURE:
<223> OTHER INFORMATION: Synthetic Primer mDnm2 (R)

<400> SEQUENCE: 45
gctgtcagca cgaaccagta        20

<210> SEQ ID NO 46
<211> LENGTH: 20
<212> TYPE: DNA
<213> ORGANISM: artificial
<220> FEATURE:
<223> OTHER INFORMATION: Synthetic Primer mDnm1 (F)

<400> SEQUENCE: 46
agatggagcg aattgtgacc        20

<210> SEQ ID NO 47
<211> LENGTH: 20
<212> TYPE: DNA
<213> ORGANISM: artificial
<220> FEATURE:
<223> OTHER INFORMATION: Synthetic Primer mDnm1 (R)

<400> SEQUENCE: 47
gaatgacctg gttccctgaa                                             20

<210> SEQ ID NO 48
<211> LENGTH: 20
<212> TYPE: DNA
<213> ORGANISM: artificial
<220> FEATURE:
<223> OTHER INFORMATION: Synthetic Primer mDnm3 (F)

<400> SEQUENCE: 48
atgctccgaa tgtaccaagc                                             20

<210> SEQ ID NO 49
<211> LENGTH: 20
<212> TYPE: DNA
<213> ORGANISM: artificial
<220> FEATURE:
<223> OTHER INFORMATION: Synthetic Primer mDnm3 (R)

<400> SEQUENCE: 49
gaggggagca cttatcgtca                                             20

<210> SEQ ID NO 50
<211> LENGTH: 20
<212> TYPE: DNA
<213> ORGANISM: artificial
<220> FEATURE:
<223> OTHER INFORMATION: Synthetic Primer mDnm2speMut (F)

<400> SEQUENCE: 50
aattgtcacc acctacatca                                             20

<210> SEQ ID NO 51
<211> LENGTH: 23
<212> TYPE: DNA
<213> ORGANISM: artificial
<220> FEATURE:
<223> OTHER INFORMATION: Synthetic Primer mDnm2speMut (R)

<400> SEQUENCE: 51
ggtttgtgtt gatgtacgac tgc                                         23

<210> SEQ ID NO 52
<211> LENGTH: 20
<212> TYPE: DNA
<213> ORGANISM: artificial
<220> FEATURE:
<223> OTHER INFORMATION: Synthetic Primer mDnm2speWT (F)

<400> SEQUENCE: 52
aattgtcacc acctacatct                                             20

<210> SEQ ID NO 53
<211> LENGTH: 23
<212> TYPE: DNA
<213> ORGANISM: artificial
<220> FEATURE:
<223> OTHER INFORMATION: Synthetic Primer mDnm2speWT (R)

-continued

<400> SEQUENCE: 53
ggtttgtgtt gatgtacgac tgc                                    23

<210> SEQ ID NO 54
<211> LENGTH: 19
<212> TYPE: DNA
<213> ORGANISM: artificial
<220> FEATURE:
<223> OTHER INFORMATION: Synthetic Primer mDnm2g (F)

<400> SEQUENCE: 54
ctgcgagagg agaccgagc                                         19

<210> SEQ ID NO 55
<211> LENGTH: 23
<212> TYPE: DNA
<213> ORGANISM: artificial
<220> FEATURE:
<223> OTHER INFORMATION: Synthetic Primer mDnm2g (R)

<400> SEQUENCE: 55
gctgagcact ggagagtgta tgg                                    23

<210> SEQ ID NO 56
<211> LENGTH: 20
<212> TYPE: DNA
<213> ORGANISM: artificial
<220> FEATURE:
<223> OTHER INFORMATION: Synthetic Primer hDnm2 (F)

<400> SEQUENCE: 56
gaaaaagcag gtcgtcaagc                                        20

<210> SEQ ID NO 57
<211> LENGTH: 18
<212> TYPE: DNA
<213> ORGANISM: artificial
<220> FEATURE:
<223> OTHER INFORMATION: Synthetic Primer hDnm2 (R)

<400> SEQUENCE: 57
attggggatg gctctctt                                          18

<210> SEQ ID NO 58
<211> LENGTH: 20
<212> TYPE: DNA
<213> ORGANISM: artificial
<220> FEATURE:
<223> OTHER INFORMATION: Synthetic Primer hHPRT (F)

<400> SEQUENCE: 58
accccacgaa gtgttggata                                        20

<210> SEQ ID NO 59
<211> LENGTH: 20
<212> TYPE: DNA
<213> ORGANISM: artificial
<220> FEATURE:
<223> OTHER INFORMATION: Synthetic Primer hHPRT (R)

<400> SEQUENCE: 59
aagcagatgg ccacagaact                                        20